(12) United States Patent
Shin et al.

(10) Patent No.: US 12,157,785 B2
(45) Date of Patent: Dec. 3, 2024

(54) POLY(ALLYL GLYCIDYL ETHER)-BASED REDOX POLYMER AND ELECTROCHEMICAL BIOSENSOR USING SAME

(71) Applicant: I-SENS, INC., Seoul (KR)

(72) Inventors: Hyunseo Shin, Seoul (KR); Bona Yang, Gyeonggi-do (KR); In Seok Jeong, Seoul (KR); Young Jea Kang, Seoul (KR)

(73) Assignee: I-SENS, INC., Seoul (KR)

( * ) Notice: Subject to any disclaimer, the term of this patent is extended or adjusted under 35 U.S.C. 154(b) by 760 days.

(21) Appl. No.: 17/276,797

(22) PCT Filed: Sep. 18, 2019

(86) PCT No.: PCT/KR2019/012084
§ 371 (c)(1),
(2) Date: Mar. 16, 2021

(87) PCT Pub. No.: WO2020/060194
PCT Pub. Date: Mar. 26, 2020

(65) Prior Publication Data
US 2022/0025114 A1 Jan. 27, 2022

(30) Foreign Application Priority Data

Sep. 18, 2018 (KR) .................. 10-2018-0111633
Sep. 17, 2019 (KR) .................. 10-2019-0114354

(51) Int. Cl.
| | | |
|---|---|---|
| *C08F 226/06* | (2006.01) | |
| *C08G 65/334* | (2006.01) | |
| *C08G 65/338* | (2006.01) | |
| *C12Q 1/00* | (2006.01) | |
| *C12Q 1/26* | (2006.01) | |
| *C12Q 1/32* | (2006.01) | |
| *G01N 27/327* | (2006.01) | |

(52) U.S. Cl.
CPC ........ *C08F 226/06* (2013.01); *C08G 65/3344* (2013.01); *C08G 65/338* (2013.01); *C12Q 1/001* (2013.01); *C12Q 1/26* (2013.01); *C12Q 1/32* (2013.01); *G01N 27/3272* (2013.01); *G01N 27/3277* (2013.01); *C08F 2810/00* (2013.01)

(58) Field of Classification Search
USPC .......................................................... 528/9
See application file for complete search history.

(56) References Cited

U.S. PATENT DOCUMENTS

| | | | |
|---|---|---|---|
| 8,828,204 B2 | 9/2014 | Mao et al. | |
| 2003/0042137 A1 | 5/2003 | Mao et al. | |
| 2008/0102441 A1 | 5/2008 | Chen et al. | |
| 2009/0294307 A1 | 12/2009 | Liu et al. | |
| 2016/0045147 A1 | 2/2016 | Ouyang et al. | |
| 2017/0096528 A1 | 4/2017 | Kee et al. | |

FOREIGN PATENT DOCUMENTS

| | | |
|---|---|---|
| JP | S62241924 A | 10/1987 |
| JP | H03210312 A | 9/1991 |
| JP | H03210364 A | 9/1991 |
| JP | H7-506674 A | 7/1995 |
| JP | 2003514924 B2 | 4/2003 |
| JP | 2006509837 A | 3/2006 |
| JP | 2010531976 A | 9/2010 |
| JP | 2020526748 A | 8/2020 |
| KR | 1020140132869 A | 11/2014 |
| KR | 101694982 B1 | 1/2017 |
| WO | 0136430 A1 | 5/2001 |
| WO | 0136660 A2 | 5/2001 |

OTHER PUBLICATIONS

Bongjae F. Lee et al. , Poly(allyl glycidyl ether)—A versatile and functional polyether platform; Journal of Polymer Science Part A: Polymer Chemistry2011, 49, 4498-4504 (Year: 2011).*
English abstract translation of JP2003514924 retrieved from https://www.j-platpat.inpit.go.jp/s0100 on Jul. 29, 2021.
Japanese Office Action for JP Application No. 2021-505661, issued on Jun. 24, 2022, 7 pages.
Extended European Search Report for European Application No. 19863300.0, issued on Aug. 5, 2022, 6 pages.
Murakami et al: "One-pot "click" fabrication of slide-ring gels"; Macromolcules; vol. 48, Oct. 26, 2015; pp. 7774-7781; XP002806990.
Aoife O'connor et al: "Poly(Ethylene Glycol)-Based Backbones with High Peptide Loading Capacities"; Molecules; vol. 19, No. 11; Oct. 30, 2014; pp. 17559-17577; XP055630501.
Hyunjae Lee et al: "Enzyme-based glucose sensor: from invasive to wearable devices"; Advanced Healthcare Materials; vol. 7, No. 8; Jan. 15, 2018; p. 1701150; XP0055762872.
Katharine W. Oleske, et al: "Nanopatterning of Crystalline Transition Metal Oxides by Surface Templated Nucleation on Block Copolymer Mesostructures"; Crystal Growth & Design; vol. 17; 2017; 8 pages.
Katharine W. Oleske, et al: "Block Copolymer Directed Nanostructured Surfaces as Templates for Confined Surface Reactions"; Macromolecules; 2017; vol. 50; 8 pages.

(Continued)

*Primary Examiner* — Terressa Boykin
(74) *Attorney, Agent, or Firm* — Polsinelli P.C.

(57) ABSTRACT

The present disclosure relates to an oxidation-reduction polymer which can be used in an electrochemical sensor, and particularly, in a polymer backbone of an electron transfer medium of the electrochemical sensor. More specifically, the present disclosure relates to: an oxidation-reduction polymer which can be used in a poly (allyl glycidyl ether)-based electrochemical sensor including a repeating unit derived from allyl glycidyl ether; and an electron transfer medium and an electrochemical sensor including same, wherein the oxidation-reduction polymer is advantageous in confirming the completion of reaction during manufacture, has high immobilization efficiency of the transition metal complex, has low possibility of having problems of toxicity and side effects, and can add various functions.

18 Claims, 3 Drawing Sheets

(56) References Cited

OTHER PUBLICATIONS

J. Christian Persson et al: "Block Copolymers Containing Intrinsically Proton-Conducting Blocks Tethered with Benzimidazole Units"; Chem Mater, Feb. 4, 2006; vol. 18; No. 13; pp. 3096-3102.
Markus J. Barthel; "Small but Powerful: Co-Assembly of Polyether-Based Triblock Terpolymers into Sub-30 nm Micelles and Synergistic Effects on Cellular Interactions"; Bio Macromolecules; vol. 15; 2014; pp. 2426-2439.
English Abstract of Japanese application JPH03-201364A, retrieved from https://worldwide.espacenet.com/ 1 page.
English Abstract of Japanese application JPH03-210312A, retrieved from https://worldwide.espacenet.com/ 1 page.
English Abstract of Japanese application JPS62-241924A, retrieved from https://worldwide.espacenet.com/ 1 page.
English Abstract of KR101694982B1 retrieved from https://worldwide.espacenet.com/ on Jun. 14, 2021.
International Search Report and Written Opinion of PCT/KR2019/006000 mailed Aug. 14, 2019.
English Translation of the International Search Report and Written Opinion of PCT/KR2019/006000 mailed Aug. 14, 2019.
Feldman B, Brazg R, Schwartz S, Weinstein R. A continuous glucose sensor based on wired enzyme technology—results from a 3-day trial in patients with type 1 diabetes. Diabetes Technol Ther. 2003;5(5):769-79. doi: 10.1089/152091503322526978. PMID: 14633342.
Zabarska N, Stumper A, Rau S. CuAAC click reactions for the design of multifunctional luminescent ruthenium complexes. Dalton Transactions (Cambridge, England : 2003). Feb. 2016;45(6):2338-2351. DOI: 10.1039/c5dt04599a.
Ohara, T.J., Osmium Bipyridyl Redox Polymers Used in Enzyme Electrodes, Platinum Metals Rev., 1995, 39, (2), 54-62.
International Search Report and Written Opinion for PCT/KR2019/012084 mailed on Jan. 10, 2020.
Translation of International Search Report for PCT/KR2019/012084 mailed on Jan. 10, 2020.
Smutok, O. et al., "A reagentless bienzyme amperometric biosensor based on alco hol oxidase/peroxidase and an Os-complex modified electrodeposition paint", Sensors and Actuators B: Chemical, 2006, vol. 113, No. 2, pp. 590-598.
Obermeier, B. et al., "Poly(ethylene glycol-co-allyl glycidyl ether)s: A PEG-based modular synthetic platform for multiple bioconjugation", Bioconjugate chemistry, 2011, vol. 22, No. 3, pp. 436-444.
Ohara, T. J., "Osmium Bipyridyl redox polymers used in enzyme electrodes", Platinum Metals Review, 1995, vol. 39, No. 2, pp. 54-62.
Long Tethers Binding Redox Centers to Polymer Backbones Enhance Electron Transport in Enzyme "Wiring" Hydrogels; J. Am. Chem. Soc. 2003, 125, 4951-4957.
Sharpless, KB, et al., Angew. Chem. Int. Ed. 40, 2001, 2004-2021.
Agnew, Chem. Int. Ed. Engl. 29 (1990) No. 1, pp. 82-84.
English Translation of KR10-2014-0132869A retrieved from http://enpat.kipris.or.kr/engpat/biblioa.do.
Japanese Office Action for JP Application No. 2021-514521, issued on Feb. 7, 2022, 3 pages.
Translation of Japanese Office Action for JP 2021-514521 mailed on Feb. 7, 2022.
English Abstract of JP2006509837 retrieved from https://worldwide.espacenet.com/ on Apr. 6, 2022.
English Abstract of JP2020526748 retrieved from https://worldwide.espacenet.com/ on Apr. 6, 2022.
English Abstract of JPH7-506674 retrieved from https://worldwide.espacenet.com/ on Apr. 6, 2022.
English Abstract of JP2010531976 retrieved from https://worldwide.espacenet.com/ on Apr. 6, 2022.

\* cited by examiner

POLY(ALLYL GLYCIDYL ETHER)-BASED REDOX POLYMER AND ELECTROCHEMICAL BIOSENSOR USING SAME

CROSS-REFERENCE TO RELATED APPLICATIONS

This application is a national stage entry of PCT/KR2019/012084 filed Sep. 18, 2019, which claims the benefit of Korean Patent Application No. 10-2018-0111633 filed on Sep. 18, 2018 and Korean Patent Application No. 10-2019-0114354 filed on Sep. 17, 2019 with Korean Intellectual Property Office, the disclosure(s) of which is incorporated herein by reference in its entirety.

TECHNICAL FIELD

The present disclosure relates to an oxidation-reduction (REDOX) polymer which can be used in an electrochemical sensor, and particularly, in a polymer backbone of an electron transfer medium of the electrochemical sensor. More specifically, the present disclosure relates to: an oxidation-reduction polymer which can be used in a poly(allyl glycidyl ether)-based electrochemical sensor comprising a repeating unit derived from allyl glycidyl ether; and an electron transfer medium and an electrochemical sensor comprising same.

BACKGROUND ART

Recently, interest in the development of biosensors is increasing day by day for quantitative and qualitative analysis of target analytes from the medical field to the environment and food fields. In particular, an enzymatic biosensor is a chemical sensor used for selectively detecting and measuring chemical substances contained in a sample by utilizing a biological sensing function in which functional substances of living organisms or organisms such as microorganisms react sensitively with a specific substance, and it has been mainly developed for medical measurement applications such as blood glucose sensors, and is also being actively studied even in applications in the fields of food engineering and environmental measurement.

Periodic measurement of blood glucose is very important in the management of diabetes. Therefore, a wide variety of blood glucose level measuring devices are being prepared so that blood glucose levels can be easily measured using a portable measuring device. The operating principle of such a biosensor is based on an optical method or an electrochemical method. Such an electrochemical biosensor can reduce the influence of oxygen, unlike a biosensor using a conventional optical method, and has the advantage that it can be used without separate pretreatment even if the sample becomes turbid. Therefore, various types of electrochemical biosensors with accuracy and precision are widely used.

Currently commercialized electrochemical blood glucose sensors mainly use enzyme electrodes. More specifically, it has a structure in which a glucose oxidase is immobilized on an electrode capable of converting an electrical signal by a chemical or physical method. These electrochemical blood glucose sensors are based on the principle of measuring the electric current generated by transferring electrons generated by the enzyme oxidation of glucose in analytes such as blood by enzymes to electrodes, thereby measuring the glucose concentration in the analyte. In the case of a biosensor using an enzyme electrode, there is a problem that since the distance from the active center of the enzyme is too far, it is not easy to transfer electrons generated by oxidation of the substrate directedly to the electrode. Therefore, in order to easily carry out such an electron transfer reaction, an oxidation-reduction medium, that is, an electron transfer medium is essentially required. Therefore, it is the type of enzyme used and the characteristics of the electron transfer medium that have the greatest influence on the characteristics of the electrochemical biosensor that measures blood sugar.

On the other hand, a continuous glucose monitoring (CGM) system is used to continuously monitor blood glucose levels and manage diseases such as diabetes, and existing enzyme sensors that collect blood from the fingertips induce a considerable pain due to a needle during blood collection and thus limits the measurement frequency and cannot be used for such CGM. In order to solve these problems, an improved version of a continuous glucose monitoring sensor that can adhere to the body and thus minimize invasion has recently been developed. In the case of such as continuous blood glucose monitoring enzyme sensor, since a part of the sensor enters the human body, in order to prevent the electron transport chain containing transition metals and the like from being absorbed by the human body and causing toxicity and side effects as described above, an attempt was made to mainly use a heterocyclic polymer containing nitrogen atoms such as poly(vinylpyridine) [PVP] or poly(vinylimidazole) (PVI] as a polymer backbone, and fix the transition metal complex via a linker, thereby preventing problems due to the loss of the electron transfer medium in the human body. However, these existing oxidation-reduction polymers have problems that the synthesis step of the final material is long and complex, the immobilization efficiency of the transition metal complex is low, and it is difficult to introduce other functionalities into the polymer, as shown in Reaction Scheme 1 below. Therefore, in order to develop oxidation-reduction polymers with excellent performance, there is a need to develop new materials beyond the limits of existing materials.

3 4
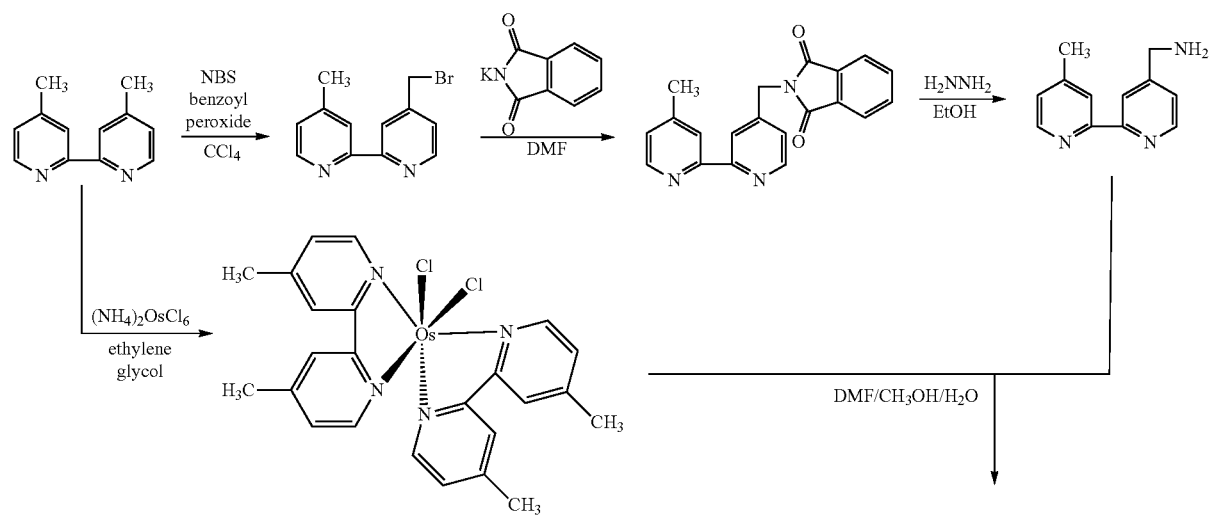
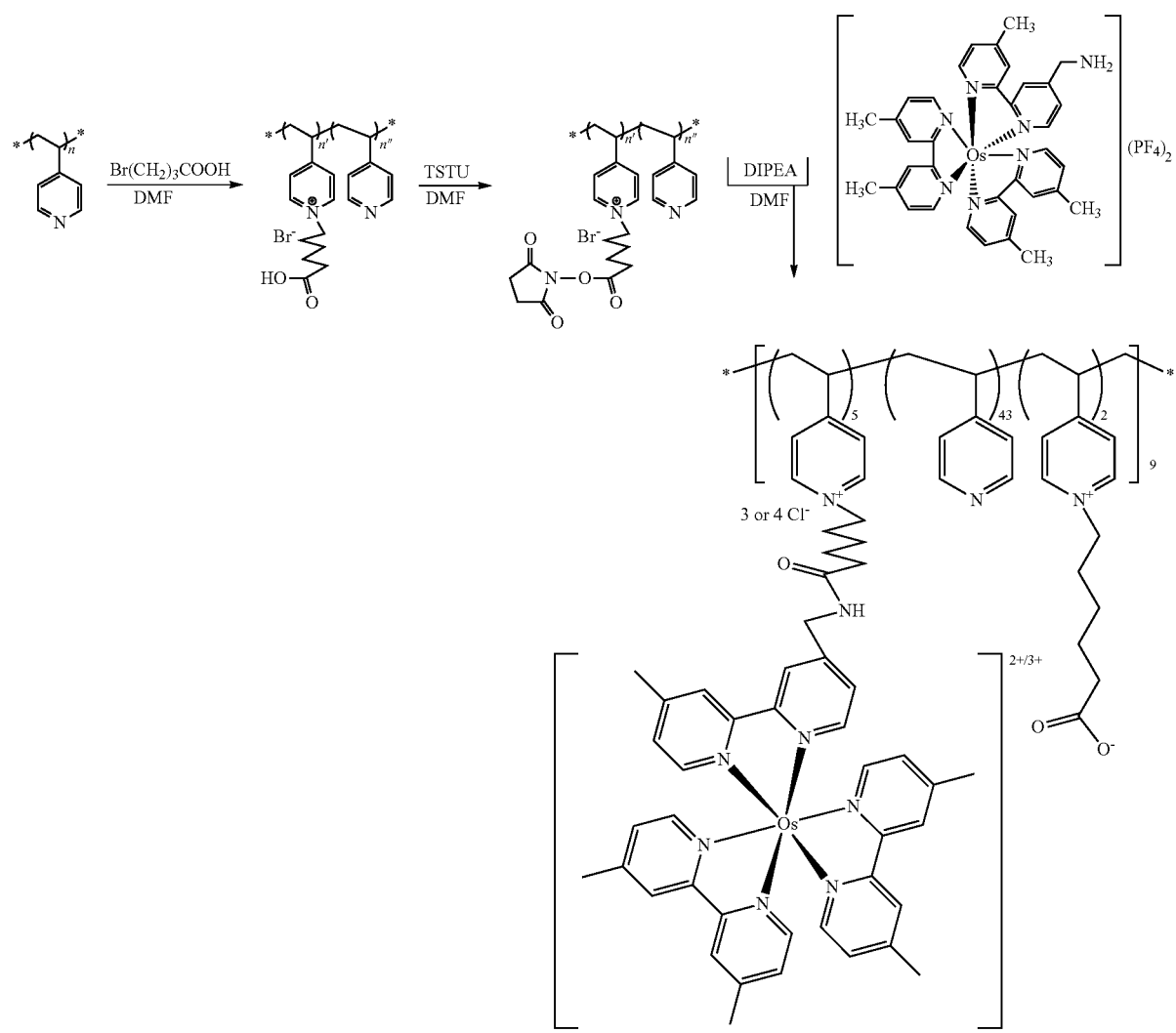

Under these circumstances, the present inventors have conducted intensive research to develop a polymer for an electron transport medium of an electrochemical sensor that satisfies the requirement that as a multifunctional oxidation-reduction polymer, the manufacturing step is relatively easy, the characteristics of the polymer main backbone can be easily controlled, and the introduction of additives imparting various functions to the polymer main skeleton should be facilitated. As a result, when using a poly(allyl glycidyl ether)-based polymer, it was unexpectedly confirmed that all of the above requirements could be excellently satisfied, thereby completing the present disclosure.

DETAILED DESCRIPTION OF THE INVENTION

Technical Problem

The present disclosure has been devised to solve the above-mentioned problems, and thus, it is an object of the present disclosure to provide a polymer precursor for the preparation of an oxidation-reduction polymer for electron transport medium, which can be prepared in a simpler step compared to a conventional method, can increase the immobilization rate of the transition metal complex while the molecular weight of the polymer can be adjusted by anion polymerization, and facilitates the introduction of a functional group or a linker, and a method for preparing the same.

It is another object of the present disclosure to provide an electron transfer medium and an electrochemical biosensor including a transition metal complex and the oxidation-reduction polymer.

Technical Solution

In order to achieve the above objects, the present disclosure provides an electron transport medium comprising a precursor for the preparation of a poly(allyl glycidyl ether)-based oxidation-reduction polymer including a repeating unit derived from allyl glycidyl ether, an oxidation-reduction polymer for high electrochemical biosensor including the precursor and a transition metal complex, and an oxidation-reduction polymer for electrochemical biosensor prepared therefrom, and an electrochemical biosensor including the same, such as a blood glucose sensor.

Advantageous Effects

When the precursor for the preparation of an oxidation-reduction polymer based on poly(allyl glycidyl ether) according to the present disclosure and an oxidation-reduction polymer including the precursor and a transition metal complex, the presence or absence of an allyl group in each repeating unit after the organic reaction using this can be relatively clearly confirmed through nuclear magnetic resonance (1H-NMR, 13C-NMR) or infrared spectroscopy (FT-IR), and thus, it is advantageous in confirming the completion of reaction during manufacture. Further, the transition metal complex can be immobilized with higher efficiency than PVP and PVI, so the problems of toxicity or side effects that may occur due to the outflow of transition metal complex are significantly lowered, and since it has the advantage that it is easy to introduce functional groups that imparts various functionalities to the backbone of the polymer and can be configured in the form of a block copolymer, and thus, is useful as an electronic medium backbone for electrochemical biosensors such as blood glucose measurement sensors.

DETAILED DESCRIPTION OF THE EMBODIMENTS

Figure 1:
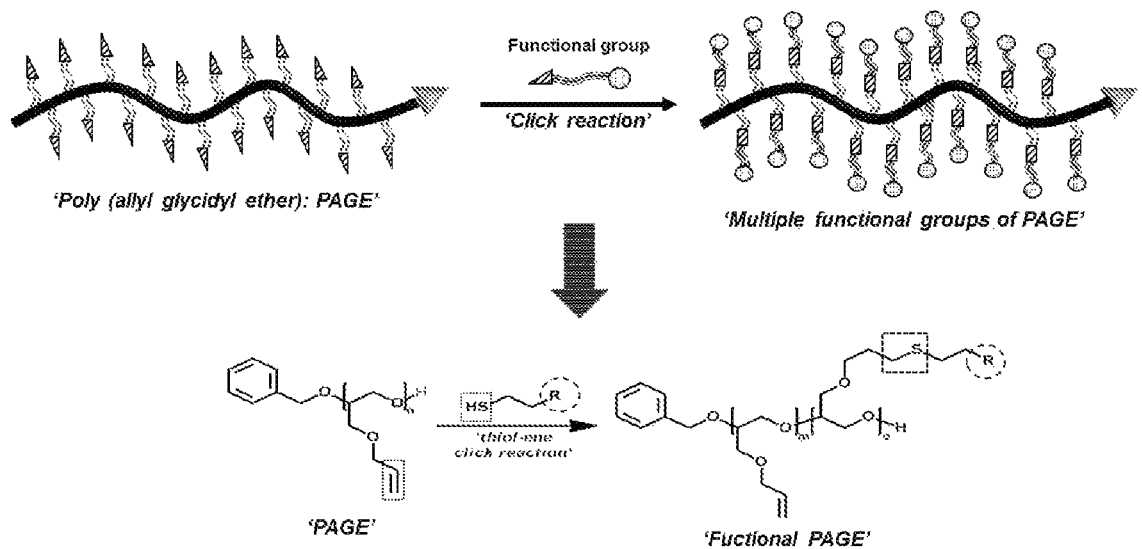
FIG. 1 is an example of bonding various functional groups to poly(allyl glycidyl ether) according to the present disclosure via a click reaction.

Hereinafter, the present disclosure will be described in more detail.

The polymer for the preparation of the oxidation-reduction polymer material according to the present disclosure is based on poly(allyl glycidyl ether), and specifically, is used as a polymer precursor of an oxidation-reduction polymer material containing a repeating unit derived from allyl glycidyl ether. Preferably, the polymer may form an oxidation-reduction polymer material for an electron transport medium together with a crosslinking material having a reactive group comprising a group selected from the group consisting of an azide group, an epoxy group and an amine group, and a transition metal complex.

Non-limiting examples of the polymer include one or more selected from the group consisting of poly(allyl glycidyl ether) (PAGE) homopolymer, poly(allyl glycidyl ether)-polymethyl methacrylate (PAGE-PMMA) copolymer, poly(allyl glycidyl ether)-polyethylene oxide (PAGE-PEO) copolymer, poly(allyl glycidyl ether)-polystyrene (PAGE-PS) copolymer, polystyrene-poly(allyl glycidyl ether)-polyethylene oxide (PS-PAGE-PEO) copolymer, and polymethyl methacrylate-poly(allyl glycidyl ether)-polyethylene oxide (PMMA-PAGE-PEO) copolymer, but are not limited thereto.

The copolymer may be an alternating copolymer, a random copolymer, a block copolymer, or a graft copolymer. For example, the copolymer may be a block copolymer. In another example, the polymer may be a diblock copolymer, such as PAGE-b-PMMA, PAGE-b-PEO, PAGE-b-PS, PAGE-b-PVP, PAGE-b-PVI or PAGE-b-PU, and the triblock copolymer may be, for example, PS-b-PAGE-b-PS, PMMA-b-PAGE-b-PMMA, PEO-b-PAGE-b-PEO, PEO-b-PAGE-PS, or PEO-b-PAGE-b-PMMA.

The poly(allyl glycidyl ether)-based polymer may have a weight average molecular weight in the range of 1,000 g/mol to 500,000 g/mol, for example, 10,000 g/mol to 20,000 g/mol.

These poly(allyl glycidyl ether)-based polymers contain an allyl group having a double bond for each repeating unit, and thus, various chemical reactive groups can be easily introduced to the side branch by a click reaction, for example, a thiol-ene reaction, and it may be cross-linked via heat treatment and subsequent processes (e.g., irradiation of light) to form an electron transport medium. In connection with the above heat treatment and subsequent processes, oxidation-reduction polymers with PVI and PVP backbone according to the prior art add an additional crosslinking material in order to finally subject to doping and immobilization on the sensor layer. In this case, there is a problem that the type of crosslinking material has no choice but to be limited to the amine-epoxy type, whereas when the poly(allyl glycidyl ether)-based polymer according to the present disclosure is used as a polymer precursor, it is easy to introduce a crosslinked material having various functional groups, and thus, various types of cross-linking reactions are possible, which is advantageous in terms of material development.

The click chemistry (reaction) is an approach first proposed by Professor Barry Sharpless of the United States in 2001 to more effectively create new substances required for new drug development (Sharpless, K B et al., Angew. Chem. Int. Ed. 40, 2001, 2004-2021), and it refers to reactions that can easily synthesize various molecules with very high selectivity and efficiency under relatively simple reaction conditions.

As a specific example, the poly(allyl glycidyl ether) in the oxidation-reduction polymer according to the present disclosure may be prepared through anionic polymerization as shown in the following Reaction Scheme 2. Typically, potassium naphthelenide is used as an initiator, without being limited thereto.

[Reaction Scheme 2]

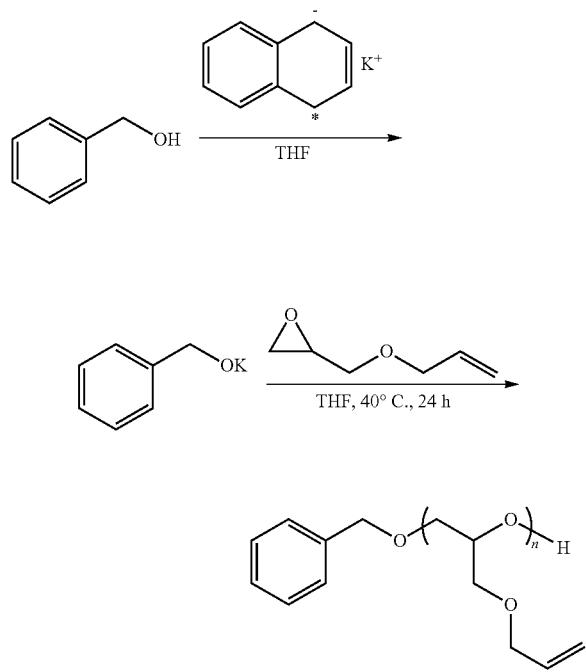

(1)

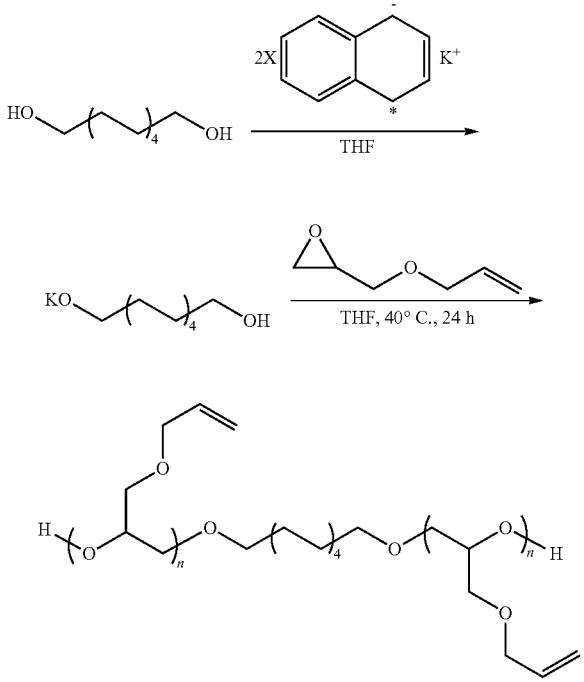

(2)

In a specific embodiment according to the present disclosure, benzyl alcohol or 1,10-decanediol is dissolved in anhydrous tetrahydrofuran under an argon atmosphere, and then, potassium naphthalenide is added dropwise as an initiator and stirred. Allyl glycidyl ether is added to the reaction mixture, stirred, and then separated and extracted to prepare poly(allyl glycidyl ether). Then, using 1-azido-11-undecanthiol, a functional group is introduced through a thiol-ene click reaction to prepare polyallyl glycidyl-based polymer.

The poly(allyl glycidyl ether)-based polymer according to the present disclosure may be a starting material for preparing an electron transport medium used in an electrochemical sensor.

Further, the poly(allyl glycidyl ether)-based polymer may be a polymer (precursor) functionalized by the introduction of a functional group selected from the group consisting of an amine group, an ammonium group, a halogen group, an epoxy group, an azide group, an acrylate group, an alkenyl group, an alkynyl group, a thiol group, an isocyanate, an alcohol group and a silane group. Introduction of such a functional group can be achieved by a crosslinking material having the functional group. As the crosslinking material, those having a functional group selected from the group consisting of an amine group, an ammonium group, a halogen group, an epoxy group, an azide group, an acrylate group, an alkenyl group, an alkynyl group, a thiol group, an isocyanate, an alcohol group and a silane group can be appropriately selected and used. Preferably, it may be a thiol-based compound having the functional group.

In a preferred embodiment, such polymer may have a structure of the following Chemical Formula 1 or 2:

[Chemical Formula 1]

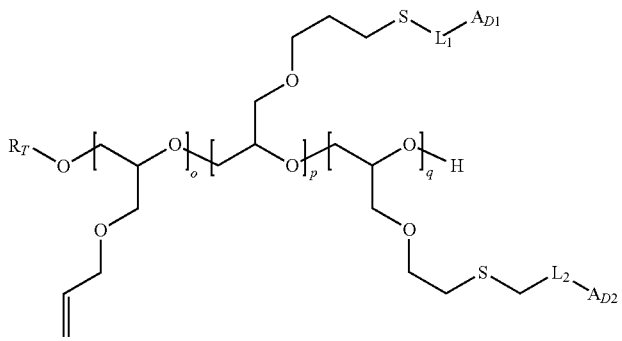

[Chemical Formula 2]

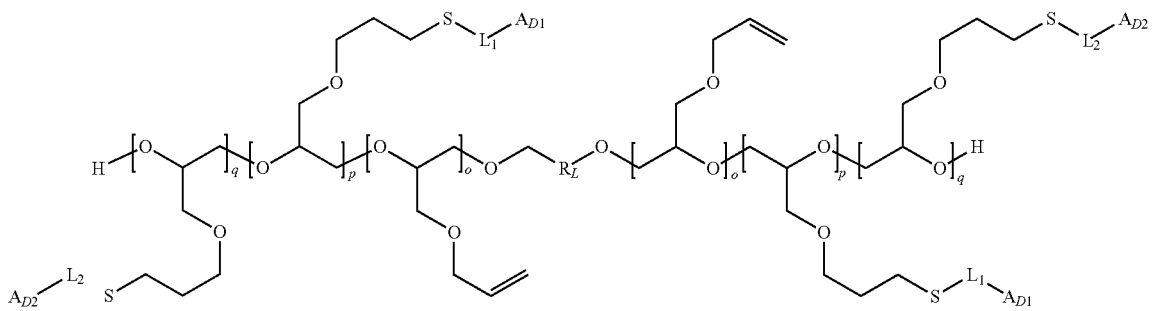

in the polymer precursor structure of Chemical Formula 1 or 2, $R_T$ and $R_L$ may be each independently selected from the group consisting of a substituted or unsubstituted alkylene group having 1 to 20 carbon atoms, a substituted or unsubstituted cycloalkylene group having 1 to 20 carbon atoms, a substituted or unsubstituted ethylene glycol group having 3 to 30 carbon atoms, a substituted or unsubstituted arylene group having 6 to 30 carbon atoms, a substituted or unsubstituted heteroarylene group having 3 to 30 carbon atoms, a substituted or unsubstituted alkenyl group having 2 to 40 carbon atoms, and a substituted or unsubstituted alkynyl group having 2 to 40 carbon atoms, and it may be also selected from the group of polymers such as polystyrene (PS), polyethylene glycol (PEG or PEO), polymethyl methacrylate (PMMA), polyvinylimidazole (PVI), polyvinylpyridine (PVP) and polysiloxane (PDMS), each having a molecular weight of 1,000 g/mol to 50,000 g/mol.

The $L_1$ to $L_2$ are each independently selected from the group consisting of a substituted or unsubstituted alkylene group having 1 to 20 carbon atoms, a substituted or unsubstituted cycloalkylene group having 1 to 20 carbon atoms, a substituted or unsubstituted ethylene glycol group having 3 to 30 carbon atoms, a substituted or unsubstituted arylene group having 6 to 30 carbon atoms, and a substituted or unsubstituted heteroarylene group having 3 to 30 carbon atoms.

$A_{D1}$ to $A_{D2}$ are selected from the group consisting of primary and secondary amine groups, an ammonium group, a halogen group, an epoxy group, an azide group, an acrylate group, an alkenyl group, an alkynyl group, thiol group, an isocyanate, an alcohol group and a silane group.

The o is an integer of 10 to 300;

the p is an integer of 0 to 300; and the q is an integer of 10 to 300.

Specifically, the method for preparing the functionalized polymer composed of Chemical Formula 1 or 2 may be performed by subjecting poly(allyl glycidyl ether) and thiol-based compounds having various reactive groups to light irradiation (UV) in the presence of a photoinitiator as shown in the following Reaction Scheme 3, without being limited thereto. The following photoinitiators may include 2,2-dimethoxy-2-phenylacetophenone (DMPA), benzoyl peroxide, 2,2-diethoxyacetophenone, 3-hydroxy acetophenone, 1-hydroxy cyclohexyl phenyl ketone, benzophenone, 2-hydroxy-2-methyl propiophenone, 2,2-diethoxy acetophenone, 2,2-dimethoxy-2-phenyl-acetophenone or combinations thereof, without being limited thereto. For example, if 2,2-dimethoxy-2-phenylacetophenone (DMPA) is used as a photoinitiator in the following reaction, as the irradiated light, for example, light in a wavelength range of 280 to 500 nm may be irradiated for 10 minutes to 4 hours to perform the reaction.

[Reaction Scheme 3]

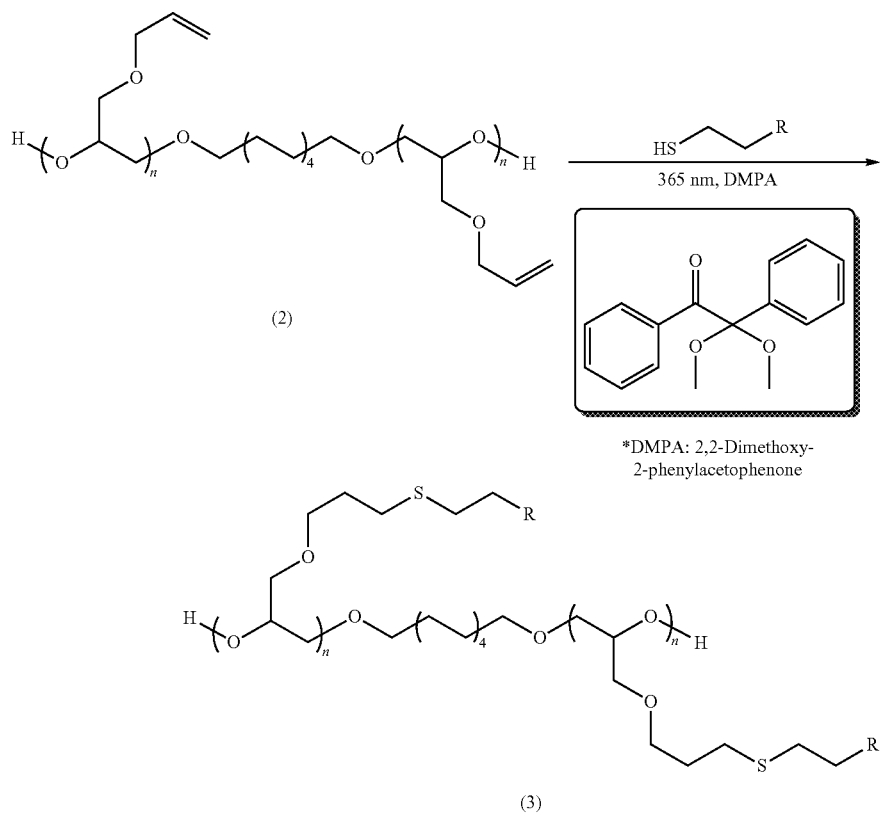

Further, the method for preparing the functionalized polymer composed of Chemical Formula 1 or 2 may be performed by reacting poly(allyl glycidyl ether) and thiol-based compounds having various reactive groups mentioned above through heat in the presence of a radical initiator (thermal initiator) as shown in the following Reaction Scheme 4, without being limited thereto. The following radical initiator may be one or more selected from 2,2'-azobisisobutyronitrile (AIBN), 2,2'-azobis-2,4-dimethyl valeronitrile, dimethyl 2,2'-azobis(isobytrate), 2,2'-azobis(4-methoxy valeronitrile), and benzoyl peroxide, without being limited thereto. For example, if AIBN is used as a radical initiator in the following reaction, as the applied heat, for example, a temperature in the range of 50 to 100° C. can be applied for 10 minutes to 12 hours to perform the reaction.

[Reaction Scheme 4]

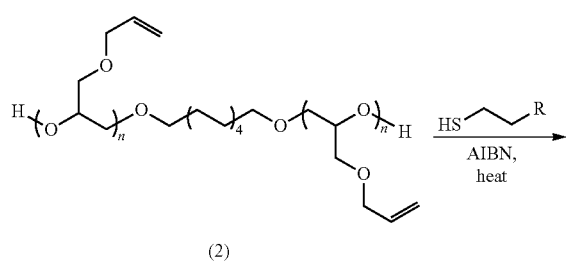

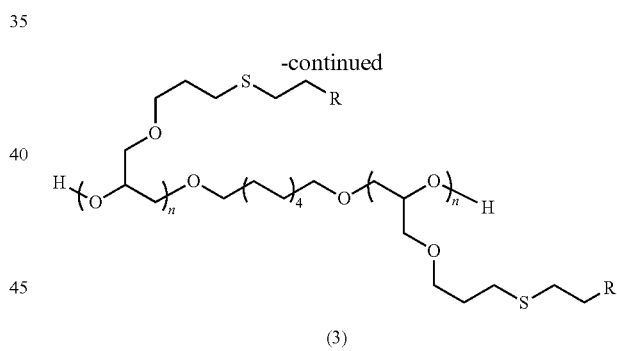

Preferably, the thiol-based compound is a thiol-based compound having, as a functional group, an azide group, an epoxy group, an acrylate group, an alkenyl group, an alkynyl group, an isocyanate, an alcohol group, a thiol group and an amine group, or a combination thereof. As used herein, the thiol-based compound refers to a compound having at least one mercapto group (—SH). More preferably, the thiol-based compound may be a compound having a structure represented by the following Chemical Formula 3.

$$HS-L_3-A_{D3} \qquad \text{[Chemical Formula 3]}$$

wherein,
the $L_3$ is independently selected from the group consisting a substituted or unsubstituted alkylene group having 1 to 20 carbon atoms, a substituted or unsubstituted cycloalkylene group having 1 to 20 carbon atoms, a substituted or unsubstituted ethylene glycol group having 3 to 30 carbon atoms, a substituted or unsubstituted arylene group having 6 to 30 carbon atoms, and a substituted or unsubstituted heteroarylene group having 3 to 30 carbon atoms, and the $A_{D3}$ is selected from the group consisting of primary and secondary amine groups, an ammonium group, a halogen group, an epoxy group, an azide group, an acrylate group, an alkenyl group, an alkynyl group, a thiol group, an isocyanate, an alcohol group and a silane group.

In another aspect, the present disclosure relates to an oxidation-reduction polymer material for an electrochemical sensor in which a transition metal complex is introduced into the poly(allyl glycidyl ether)-based polymer.

For example, such an oxidation-reduction polymer material may also be prepared by a process in which a compound containing a functional group selected from the group consisting of an amine group, an ammonium group, a halogen group, an epoxy group, an azide group, an acrylate group, an alkenyl group, an alkynyl group, a thiol group, an isocyanate, an alcohol group, and a silane group is introduced and functionalized into the poly(allyl glycidyl ether)-based polymer by a click reaction such as a thiol-ene reaction as described above, and the transition metal complex is bound to the transition metal complex by a click reaction such as azide-alkyne Huisgen cycloaddition or thiol-ene reaction.

Further, the oxidation-reduction polymer material may also be prepared by a process in which, instead of functionalizing the poly(allyl glycidyl ether)-based polymer, a functional group like a crosslinking material such as an amine group, an ammonium group, a halogen group, an epoxy group, an azide group, an acrylate group, an alkenyl group, an alkynyl group, a thiol group, an isocyanate, an alcohol group, and a silane group is introduced and functionalized into the bidentate ligand of the transition metal complex through a substitution reaction and an addition reaction, and the functionalized transition metal complex and the poly(allyl glycidyl ether)-based polymer may be bound by a click reaction.

Alternatively, the polymer material may be prepared by functionalizing both a polyallylglycidyl ether-based polymer and a transition metal complex using the crosslinking material and bonding them to each other by a click reaction.

Preferably, the transition metal complex capable of bonding to the poly(allyl glycidyl ether)-based polymer may have a structure represented by the following Chemical Formula 4:

[Chemical Formula 4]

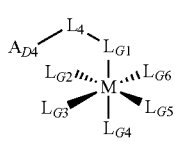

wherein,

M is a transition metal selected from the group consisting of Os, Rh, Ru, Ir, Fe and Co;

$L_{G1}$ and $L_{G2}$ are combined with each other to form a bidentate ligand selected from the following Chemical Formulas 5 to 7;

$L_{G3}$ and $L_{G4}$ are combined with each other to form a bidentate ligand selected from the following Chemical Formulas 5 to 7;

$L_{G5}$ and $L_{G6}$ are each combined with each other to form a bidentate ligand selected from the following Chemical Formulas 5 to 7;

[Chemical Formula 5]

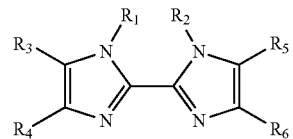

[Chemical Formula 6]

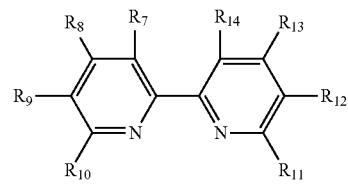

[Chemcial Formula 7]

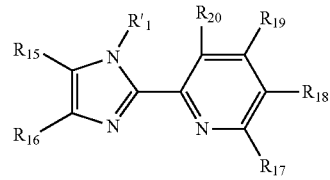

the $R_1$, $R_2$ and $R'_1$ are each independently selected from the group consisting of a substituted or unsubstituted alkyl group having 1 to 10 carbon atoms, a substituted or unsubstituted ethylene glycol group having 2 to 20 carbon atoms, a substituted or unsubstituted alcohol group having 1 to 20 carbon atoms, a substituted or unsubstituted alkylhalogen group having 1 to 20 carbon atoms, a substituted or unsubstituted thiol group having 1 to 20 carbon atoms, a substituted or unsubstituted alkyl azide group having 3 to 20 carbon atoms, a substituted or unsubstituted aryl azide group having 7 to 30 carbon atoms, a substituted or unsubstituted alkenyl group having 2 to 40 carbon atoms, a substituted or unsubstituted alkynyl group having 2 to 40 carbon atoms, a cyano group, a halogen group, deuterium and hydrogen, the $R_3$ to $R_{20}$ are each independently selected from the group consisting of a substituted or unsubstituted alkyl group having 1 to 10 carbon atoms, a substituted or unsubstituted cycloalkyl group having 3 to 40 carbon atoms, a substituted or unsubstituted aryl group having 6 to 50 carbon atoms, a substituted or unsubstituted heteroaryl group having 3 to 50 carbon atoms, a substituted or unsubstituted alkoxy group having 1 to 20 carbon atoms, a substituted or unsubstituted alcohol group having 1 to 20 carbon atoms, a substituted or unsubstituted alkylhalogen group having 1 to 20 carbon atoms, a substituted or unsubstituted thiol group having 1 to 20 carbon atoms, a substituted or unsubstituted alkyl azide group having 3 to 20 carbon atoms, a substituted or unsubstituted aryl azide group having 7 to 30 carbon atoms, a substituted or unsubstituted aryloxy group having 6 to 30 carbon atoms, a substituted or unsubstituted alkylamino group having 1 to 20 carbon atoms, a substituted or unsubstituted arylamino group having 6 to 30 carbon atoms, a substituted or unsubstituted alkylsilyl group having 1 to 20 carbon atoms, a substituted or unsubstituted arylsilyl group having 6 to 30 carbon atoms, a substituted or unsubstituted arylalkylamino group having 1 to 50 carbon atoms, a substituted or unsubstituted alkenyl group having 2 to 40 carbon atoms, a substituted or unsubstituted alkynyl group having 2 to 40 carbon atoms, a cyano group, a halogen group, deuterium and hydrogen;

the $L_4$ is independently selected from the group consisting of a substituted or unsubstituted alkylene group having 1 to 20 carbon atoms, a substituted or unsubstituted cycloalkylene group having 1 to 20 carbon atoms, a substituted or unsubstituted ethylene glycol group having 2 to 30 carbon atoms, a substituted or unsubstituted arylene group having 6 to 30 carbon atoms, and a substituted or unsubstituted heteroarylene group having 3 to 30 carbon atoms, and the $A_{D4}$ is selected from the group consisting of an azide group, an acrylate group, an alkenyl group, an alkynyl group, a thiol group, isocyanate, an alcohol group and a silane group.

In addition, the functionalized transition metal complex may have, for example, a structure of the following Chemical Formula 8a, 8b or 8c:

[Chemical Formula 8a]

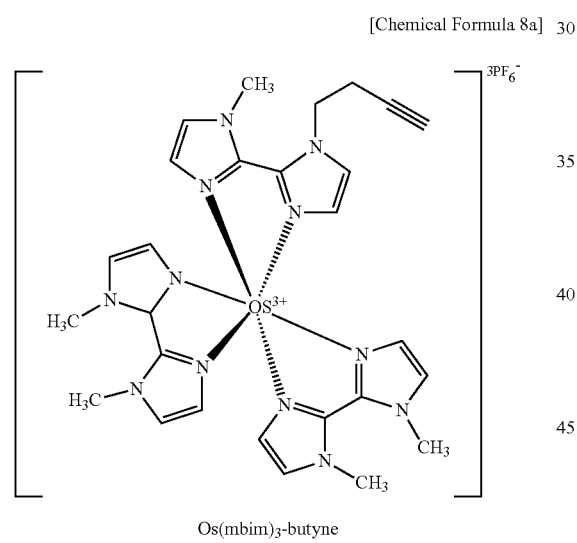

Os(mbim)$_3$-butyne

[Chemical Formula 8b]

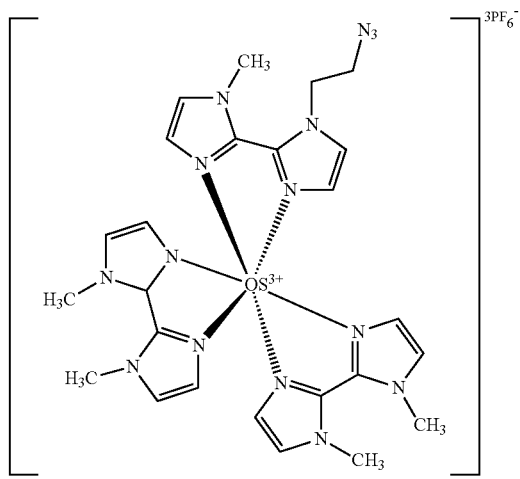

Os(mbim)$_3$-ethylazide

[Chemical Formula 8c]

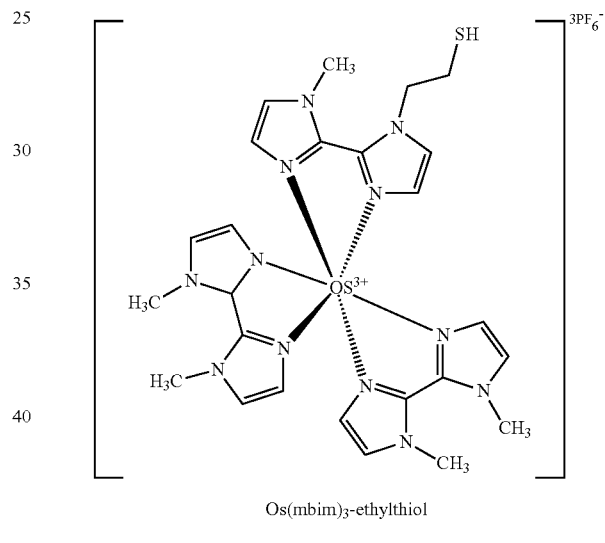

Os(mbim)$_3$-ethylthiol

In one specific example, as a preparation example of an oxidation-reduction polymer material, the functionalized polyallylglycidyl ether polymer (6) and Os(mbim)$_3$ (8a) can be synthesized into an oxidation-reduction polymer of compound (7) via a click reaction under a copper catalyst as shown in the following Reaction Scheme 4.

[Reaction Scheme 4]

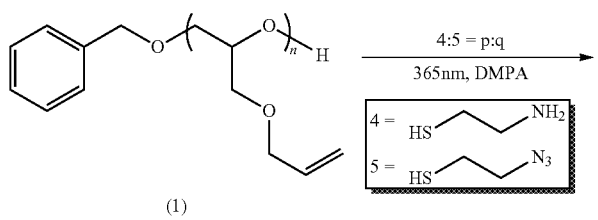

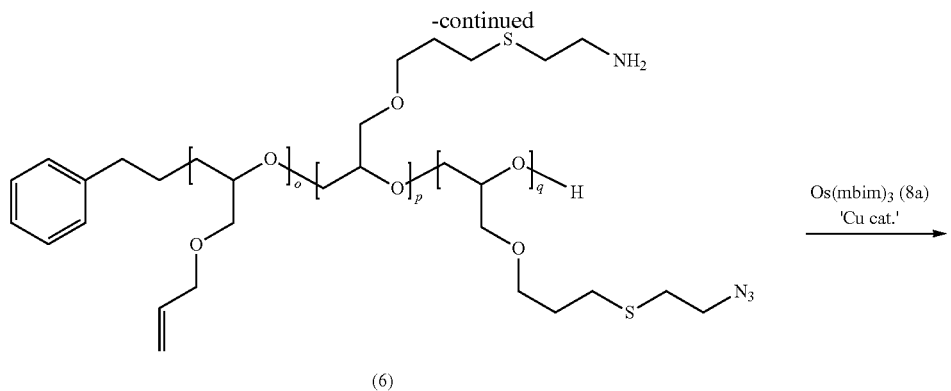

(6)

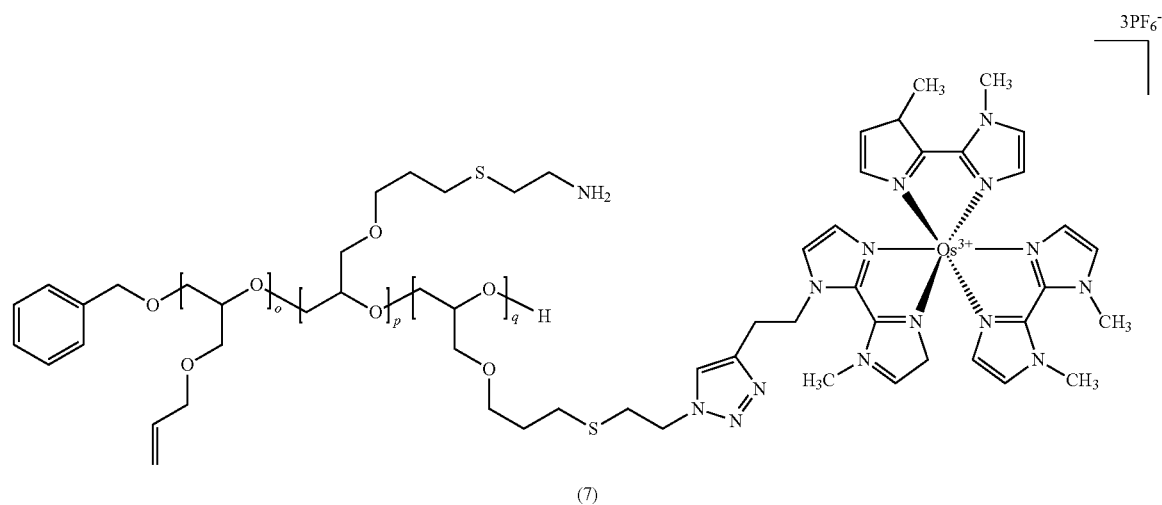

(7)

Preferably, the oxidation-reduction polymer for an electrochemical sensor in which a functional group selected from the group consisting of an amine group, an ammonium group, a halogen group, an epoxy group, an azide group, an acrylate group, an alkenyl group, an alkynyl group, a thiol group, isocyanate, an alcohol group, and a silane group, and a transition metal complex are introduced in the poly(allyl glycidyl ether)-based polymer according to the present disclosure may have a structure of the following Chemical Formula 9 or 10:

[Chemical Formula 9]

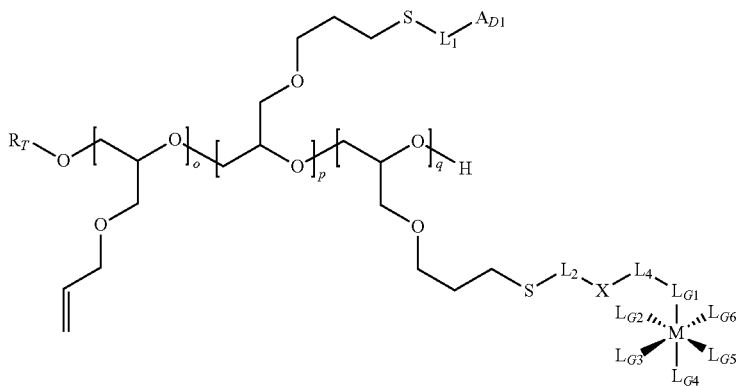

[Chemical Formula 10]

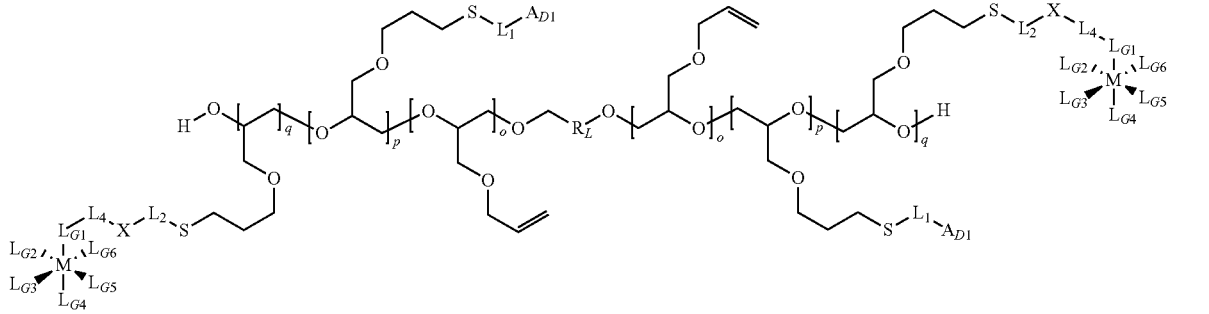

in the polymer of Chemical Formula 9 or 10, $R_T$ and $R_L$ may be each independently selected from the group consisting of a substituted or unsubstituted alkylene group having 3 to 20 carbon atoms, a substituted or unsubstituted cycloalkylene group having 6 to 20 carbon atoms, a substituted or unsubstituted ethylene glycol group having 2 to 30 carbon atoms, a substituted or unsubstituted arylene group having 6 to 30 carbon atoms, a substituted or unsubstituted heteroarylene group having 3 to 30 carbon atoms, a substituted or unsubstituted alkenyl group having 2 to 40 carbon atoms and a substituted or unsubstituted alkynyl group having 2 to 40 carbon atoms. Further, preferably, it may be selected from the group of polymers such as polystyrene (PS), polyethylene glycol (PEG) or polyethylene oxide (PEO) having a molecular weight of 1,000 g/mol to 50,000 g/mol, polymethylmethacrylate (PMMA), polyvinylimidazole (PVI), polyvinylpyridine (PVP), and polysiloxane (PDMS).

The $L_1$, $L_2$ to $L_4$ are each independently selected from the group consisting of a substituted or unsubstituted alkylene group having 1 to 20 carbon atoms, a substituted or unsubstituted cycloalkylene group having 1 to 20 carbon atoms, a substituted or unsubstituted ethylene glycol group having 3 to 30 carbon atoms, a substituted or unsubstituted arylene group having 6 to 30 carbon atoms, and a substituted or unsubstituted heteroarylene group having 3 to 30 carbon atoms.

The $A_{D1}$ is selected from the group consisting of primary and secondary amine groups, an ammonium group, a halogen group, an epoxy group, an azide group, an acrylate group, an alkenyl group, an alkynyl group, a thiol group, isocyanate, an alcohol group and a silane group.

The o is an integer of 0 to 300;
the p is an integer of 0 to 300; and
the q is an integer of 10 to 300.

Further, X may be a functional group selected from the group consisting of a triazole group, ether, thiol ether, an amide group, an urea group, an urethane group and a silane group.

M is a transition metal selected from the group consisting of Os, Rh, Ru, Ir, Fe, and CO;

$L_{G1}$ and $L_{G2}$ are combined with each other to form a bidentate ligand selected from Chemical Formulas 5 to 7;

$L_{G3}$ and $L_{G4}$ are each combined with each other to form a bidentate ligand selected from Chemical Formulas 5 to 7; and $L_{G5}$ and $L_{G6}$ are each combined with each other to form a bidentate ligand selected from Chemical Formulas 5 to 7.

Despite the introduction of a reactive group and the like when using polymers such as PVP and PVI according to the prior art, it has the disadvantage that it is difficult to confirm whether the reaction is completely completed. When the poly(allyl glycidyl ether)-based polymer according to the present disclosure is used, the allyl group which is a repeating unit disappears after the reaction, and the completion of the reaction can be clearly confirmed. Therefore, it has the advantage of being advantageous during manufacture. Further, the transition metal complex can be immobilized with higher efficiency than PVP and PVI, so the problems of toxicity or side effects that may occur due to the outflow of transition metal complex are significantly lowered, and it has the advantage that it is easy to introduce functional groups that imparts various functions to the backbone of the polymer and can be configured in the form of a block copolymer, The oxidation-reduction polymer material according to the present disclosure may be applied or laminated on the working electrode or may be located around the working electrode (for example, a structure surrounding the electrode in a solution) to transfer electrons between the working electrode and the substance to be analyzed via an enzyme. The oxidation-reduction polymer material can form non-filterable coatings on the working electrode within the electrochemical biosensor.

Therefore, a further embodiment of the present disclosure relates to a method for producing a poly(allyl glycidyl ether)-based oxidation-reduction polymer material comprising the steps of:

(a) polymerizing allyl glycidyl ether in the presence of an initiator to prepare a polyallyl-glycidyl ether-based polymer precursor; and (b) introducing a functional group selected from the group consisting of an amine group, an ammonium group, a halogen group, an epoxy group, an azide group, an acrylate group, an alkenyl group, an alkynyl group, a thiol group, an isocyanate, an alcohol group, and a silane group, and a transition metal complex into the polymer precursor prepared in step (a).

In the step (a), the initiator may be benzyl alcohol or 1,10-decanediol.

In step (b), the functional group selected from the group consisting of an amine group, an ammonium group, a halogen group, an epoxy group, an azide group, an acrylate group, an alkenyl group, an alkynyl group, a thiol group, isocyanate, an alcohol group, and a silane group may be preferably introduced using a thiol-based compound having such a functional group.\

Further, as an additional aspect, the present disclosure relates to a method of manufacturing an electron transport medium comprising the steps of: coating the poly(allyl glycidyl ether)-based oxidation-reduction polymer material onto an electrode and then curing the coated electrode.

In addition, a further embodiment of the present disclosure relates to a sensing layer for an electrochemical biosensor comprising an enzyme capable of subjecting a liquid biological sample and an electron transfer medium formed of the oxidation-reducing polymer material to an oxidation-reduction reaction, and the oxidation-reduction polymer material.

The oxidoreductase is a generic term for an enzyme that catalyzes the redox reaction in a living organism. In the case of a target substance to be measured in the present disclosure, such as a biosensor, the oxidoreductase refers to an enzyme that is reduced by reacting with a target substance to be measured. The enzyme reduced in this way reacts with the electron transport medium and generate signal such as current change, and the metabolite is quantified by measuring the signal such as the current change occurring at this time. The oxidoreductase usable in the present disclosure may be at least one selected from the group consisting of various dehydrogenase, oxidase, esterase, and the like. Depending on the redox reaction or detection target material, an enzyme using the substrate as the target material may be selected and used among enzymes belonging to the enzyme group.

More specifically, the oxidoreductase may be one or more selected from the group consisting of glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase, bilirubin oxidase, and the like.

Meanwhile, the oxidoreductase can also include a cofactor that plays a role of storing hydrogen deprived by the oxidoreductase from the target substance (e.g., metabolite) to be measured. For example, the cofactor may be one or more selected from the group consisting of flavin adenine dinucleotide (FAD), nicotinamide adenine dinucleotide (NAD), pyrroloquinoline quinone (PQQ) and the like.

For examples, when measuring the blood glucose concentration, glucose dehydrogenase (GDH) may be used as an oxidoreductase, and may include flavin adenine dinucleotide-glucose dehydrogenase (FAD-GDH) containing FAD as the cofactor and/or nicotinamide adenine dinucleotide-glucose dehydrogenase containing FAD-GDH as the cofactor.

In a specific embodiment, the available oxidoreductase may be at least one selected from the group consisting of FAD-GDH (e.g., EC 1.1.99.10 etc.), NAD-GDH (e.g., EC 1.1.1.47 etc.), PQQ-GDH (e.g., EC1.1.5.2 etc.), glutamate dehydrogenase (e.g., EC 1.4.1.2 etc.), glucose oxidase (e.g., EC 1.1.3.4 etc.), cholesterol oxidase (e.g., EC 1.1.3.6 etc.), cholesterol esterase (e.g., EC 3.1.1.13 etc.), lactate oxidase (e.g., EC 1.1.3.2 etc.), ascorbic acid oxidase (e.g., EC 1.10.3.3 etc.), alcohol oxidase (e.g., EC 1.1.3.13 etc.), alcohol dehydrogenase (e.g., EC 1.1.1.1 etc.), bilirubin oxidase (e.g., EC 1.3.3.5 etc.), and the like.

Most preferably, the oxidoreductase is a glucose dehydrogenase capable of maintaining an activity of 70% or more for 1 week in a buffer solution at 37° C.

The sensing layer according to the present disclosure may contain 20 to 700 parts by weight, for example, 60 to 700 parts by weight or 30 to 340 parts by weight of an oxidation-reduction polymer, based on 100 parts by weight of the oxidoreductase. The content of the oxidation-reduction polymer may be appropriately adjusted in accordance with the activity of the oxidoreductase.

Further, the sensing layer according to the present disclosure may further include a carbon nanotube to increase film performance. Specifically, when carbon nanotubes are used with a transition metal complex, particularly osmium, the electron transfer rate is increased and so the performance of the sensing layer can be further improved.

In addition, the sensing layer according to the present disclosure may further include a crosslinking agent.

Meanwhile, the sensing layer according to the present disclosure may further include one or more additives selected from the group consisting of surfactants, water-soluble polymers, quaternary ammonium salts, fatty acids, thickeners, etc., for the role of a dispersant during reagent dissolution, an adhesive during reagent production, a stabilizer for long-term storage, and the like.

The surfactant may play a role in allowing the composition to spread evenly over the electrodes and be dispensed with a uniform thickness when dispensing the reagents. As the surfactant, at least one selected from the group consisting of Triton X-100, sodium dodecyl sulfate, perfluorooctane sulfonate, sodium stearate, etc. may be used. In order to properly perform the role of spreading the reagent uniformly on the electrodes and dispensing the reagent with uniform thickness when dispensing the reagent, the reagent composition according to the present disclosure may contain the surfactant in an amount of 3 to 25 parts by weight, for example 10 to 25 parts by weight, based on 100 parts by weight of the oxidoreductase. For example, when using an oxidoreductase with an activity of 700 U/mg, the reagent composition may contain 10 to 25 parts by weight of a surfactant based on 100 parts by weight of the oxidoreductase. When the activity of the oxidoreductase is higher than that, the content of the surfactant can be adjusted to lower level.

The water-soluble polymer may serve to stabilize and disperse enzymes as a polymer support for the reagent composition. The water-soluble polymers used herein may include at least one selected from the group consisting of polyvinyl pyrrolidone (PVP), polyvinyl alcohol (PVA), polyfluoro sulfonate, hydroxyethyl cellulose (HEC), and hydroxypropyl cellulose (HPC), carboxy methyl cellulose (CMC), cellulose acetate, polyamide, and the like. The reagent composition according to the present disclosure may contain the water-soluble polymer in an amount of 10 to 70 parts by weight, for example 30 to 70 parts by weight based on 100 parts by weight of the oxidoreductase, in order to sufficiently and appropriately exhibit the role of assisting the stabilization and dispersing of oxidoreductase. For example, when using an oxidoreductase having an activity of 700 U/mg, the composition may contain 30 to 70 parts by weight of a water-soluble polymer based on 100 parts by weight of the oxidoreductase. If the activity of the oxidoreductase is higher than that, the content of the water-soluble polymer can be adjusted to lower level.

The water-soluble polymer may have a weight average molecular weight of about 2,500 g/mol to 3,000,000 g/mol, for example, about 5,000 g/mol to 1,000,000 g/mol, in order to effectively assist the stabilization and dispersion of a support and an enzyme.

The thickener serves to firmly adhere the reagent to the electrode. As the thickener, at least one selected from the group consisting of natrosol, diethylaminoethyl-dextran hydrochloride, and the like may be used. The electrochemical sensor according to the present disclosure may contain the thickener in an amount of 10 to 90 parts by weight, for example, 30 to 90 parts by weight, based on 100 parts by weight of the oxidoreductase, in order to ensure that the oxidation-reduction polymer according to the present disclosure is firmly attached to the electrode. For example, when using an oxidoreductase having an activity of 700 U/mg, it may contain 30 to 90 parts by weight of a thickener based on 100 parts by weight of the oxidoreductase, and when the activity of the oxidoreductase is higher than that, the content of the thickener can be adjusted to lower level.

In another embodiment, the present disclosure provides an electrochemical biosensor including an electron transport medium composed of the oxidation-reduction polymer material.

Specifically, the type of the electrochemical biosensor is not limited, but a continuous blood glucose monitoring sensor can be preferably used.

In the configuration of such a continuous blood glucose monitoring sensor, the present disclosure may include, for example, an electrode, an insulator, a substrate, a sensing layer, a diffusion layer, a protection layer, and the like which include the oxidation-reduction polymer and the oxidoreductase. In the case of an electrode, it may include two types of electrodes such as a working electrode and a counter electrode, and it may also include three types of electrodes such as a working electrode, a counter electrode, and a reference electrode. In one embodiment, the biosensor according to the present disclosure may be an electrochemical biosensor prepared by coating a reagent composition containing an electron transfer medium and an enzyme capable of subjecting a liquid biological sample to an oxidization-reduction, onto a substrate having at least two, preferably two or three electrodes, and then drying it. For example, there is provided a planar electrochemical biosensor, characterized in that in the electrochemical biosensor, an working electrode and a counter electrode are provided on opposite surfaces of a substrate, and a sensing layer containing the oxidation-reduction polymer according to the present disclosure is stacked on the working electrode, and an insulator, a diffusion layer and a protective film are sequentially stacked on both sides of a substrate having an working electrode and a counter electrode.

In a specific embodiment, the substrate may be made of one or more materials selected from the group consisting of polyethylene terephthalate (PET), polycarbonate (PC), and polyimide (PI).

Further, as the working electrode, a carbon, gold, platinum, silver or silver/silver chloride electrode may be used.

Further, in the case of an electrochemical biosensor having a 2-electrode, since the counter electrode performs up to the role of a reference electrode, gold, platinum, silver or silver/silver chloride electrodes can be used as the counter electrode. In the case of a 3-electrode electrochemical biosensor including up to the reference electrode, a gold, platinum, silver, or silver/silver chloride electrode may be used as the reference electrode, and a carbon electrode may be used as the counter electrode.

Nafion, cellulose acetate, silicone rubber, and the like can be used as the diffusion layer, and silicone rubber, polyurethane, polyurethane-based copolymer, and the like can be used as the protective layer, without being limited thereto.

As a non-limiting example, in the case of the 2-electrode, silver chloride or silver may be used because the counter electrode performs up to the role of the reference electrode, and in the case of the 3-electrode, silver chloride or silver may be used as the reference electrode, and a carbon electrode may be used as the counter electrode.

EXAMPLE

Example 1: Synthesis of Poly(Allyl Glycidyl Ether) (PAGE)

1-1: Synthesis of Type 1 polyallylglycidyl Ether (P-1)

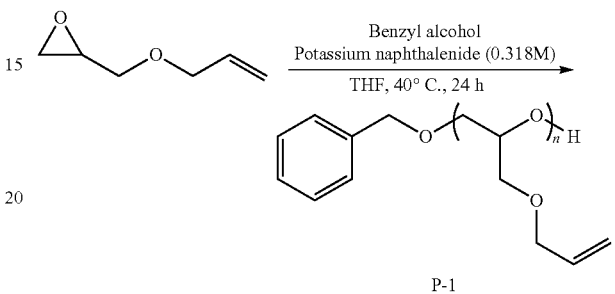

Benzyl alcohol (0.11 g, 1.0 mmol) was dissolved in 50 mL of anhydrous tetrahydrofuran under an argon atmosphere, and then potassium naphthalenide (0.25 M in tetrahydrofuran, 4.0 mL, 1.0 mmol) solution was slowly added dropwise until the solution became green as a whole, and stirred at room temperature for about 5 minutes. Allyl glycydyl ether (10.0 mL, 87.6 mol) was quickly added to the reaction mixture under an argon atmosphere, and stirred at 40° C. After 24 hours, a small amount of methanol was added to terminate the reaction, to which 10% hydrochloric acid solution and water (30 mL) were added, and the aqueous layer was separated from the organic layer, and extracted five times with dimethylene chloride (60 mL). The extracted organic layers were collected, and the solvent was removed under reduced pressure, and washed five times with hexane (10 mL) to obtain a purified polymer P-1.

$^1$H NMR (400 MHz, CDCl$_3$): δ 5.93-5.83 (m), 5.27-5.13 (m), 3.98 (br m), 3.64-3.43 (br m), 1.58 (br m), 1.32 br m) (weight recovery rate: 55%, 5.5 g)

1-2: Synthesis of Type 2 polyallylglycidyl Ether (P-2)

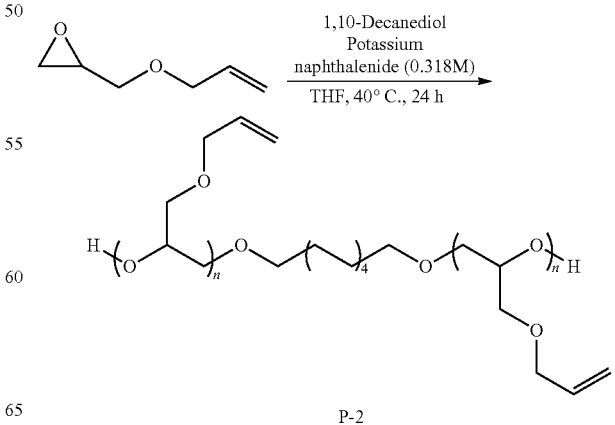

1,10-decanediol (0.23 g, 1.3 mmol) was dissolved in 100 mL of anhydrous tetrahydrofuran under an argon atmosphere, and then potassium naphthalenide (0.32 M in tetrahydrofuran, 9.0 mL, 2.9 mmol) solution was slowly added dropwise until the solution became green as a whole, and stirred at room temperature for about 5 minutes. Allyl glycydyl ether (31 mL, 0.26 mol) was quickly added to the reaction mixture under an argon atmosphere, and stirred at 40° C. After 24 hours, a small amount of methanol was added to terminate the reaction, to which 10% hydrochloric acid solution and water (30 mL) were added, and the aqueous layer was separated from the organic layer, and extracted five times with dimethylene chloride (60 mL). The extracted organic layers were collected, and the solvent was removed under reduced pressure, and washed five times with hexane (10 mL) to obtain a purified polymer P-2.

$^1$H NMR (400 MHz, CDCl$_3$): δ 5.93-5.83 (m), 5.27-5.13 (m), 3.98 (br m), 3.64-3.43 (br m), 1.58 (br m), 1.32 br m) (weight recovery rate: 76%, 18.6 g)

1-3: Introduction of Functional Group into Type 1 PAGE (P-1) Via Thiol-Ene Click Reaction

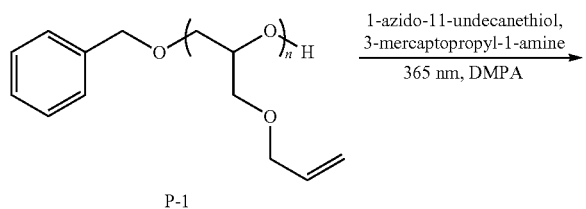

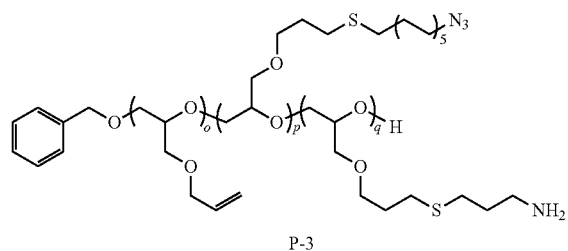

P-1 (Mn=10,000 g/mol, 1.0 g, 8.7 mmol (number of moles of allyl group in PAGE), 1-azido-11-undecanthiol (0.30 g, 1.3 mmol), 3-mercaptopropyl-1-amine (0.15 g, 1.3 mmol), and DMPA (11 mg, 0.04 mmol) were dissolved in 5 mL of benzene under an argon atmosphere, and then degassed under argon for 5 minutes. The reaction mixture was placed in a UV reactor and irradiated with light of 315 to 400 nm for 30 minutes. After completion of the reaction, the solvent was removed under reduced pressure, and washed five times with hexane/ethyl acetate (10/1) to remove the remaining starting material. Finally, a purified polymer P-3 was obtained.

$^1$H NMR (500 MHz, CDCl$_3$): δ 3.60-3.49 (br m), 2.57-2.50 (br m), 1.83 (br m), 1.69 (br m), 1.24-1.20 (br m)

Example 2: Synthesis of Osmium Complex 2-1: Synthesis of Ligand 2-1-1: Synthesis of 2,2'-biimidazole

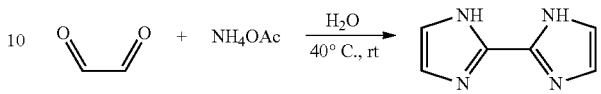

79 mL (0.69 mol) of 40% glyoxal aqueous solution was added to a 1 L three-neck round-bottom flask, cooled to 0° C., and then 370 mL (2.76 mol) of ammonium acetate was slowly added dropwise through a dropping funnel for 3 hours, while paying attention to temperature rise (less than 30° C.). After completion of the dropwise addition, the mixture was stirred overnight at 45~50° C., and then cooled to room temperature. The resulting solid was filtered, then dissolved in ethyl glycol, and purified by a hot-filter. Finally, 2,2'-biimidazole was obtained. (10.1 g, yield: 33%)

2-1-2. Synthesis of N-methyl-2,2'-biimidazole

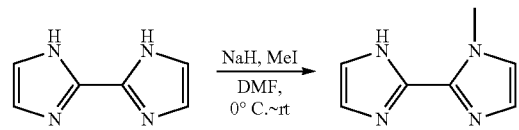

2.0 g (15 mmol) of 2,2'-biimidazole was added to a 250 mL three-neck round-bottom flask, dissolved in 60 mL of anhydrous dimethylformamide, and then cooled to 0° C. 0.6 g (15 mmol) of sodium hydride was added little by little, while paying attention to temperature rise. The mixture was stirred at 0° C. for 1 hour, and then 1 mL (15 mmol) of iodomethane was slowly added dropwise through a syringe pump. After completion of the dropwise addition, the mixture was stirred at room temperature for 12 hours. 100 mL of ethyl acetate was added to the final reaction solution, and the resulting sodium iodide was removed by filtration. The filtrate was concentrated under reduced pressure to remove all the solvent, and then the remaining solid was purified by column chromatography using ethyl acetate and hexane as developing solvents. Finally, N-methyl-2,2'-biimidazole was obtained. (0.8 g, yield: 37%)

2-1-3. Synthesis of N,N'-dimethyl-2,2'-biimidazole

5 g (37 mmol) of 2,2'-biimidazole was added to a 500 mL three-neck round-bottom flask, dissolved in 60 mL of anhydrous dimethylformamide, and then cooled to 0° C. 3 g (40 mmol) of sodium hydride was added little by little, while paying attention to temperature rise. The mixture was stirred at 0° C. for 1 hour, and then 2.5 mL (40 mmol) of iodomethane was slowly added dropwise through a syringe pump, and then stirred at room temperature for 24 hours. Water was added to the final reaction solution, extracted with ethyl acetate (200 mL×3), and then the organic layer was collected and dried over magnesium sulfate. The organic layer was concentrated under reduced pressure to remove the solvent, and then purified by column chromatography using ethyl acetate and hexane as developing solvents. Finally, N,N'-dimethyl-2,2'-biimidazole was obtained. (5.1 g, yield: 84%)

2-1-4. Synthesis of S-(6-bromohexyl)ethanethioate

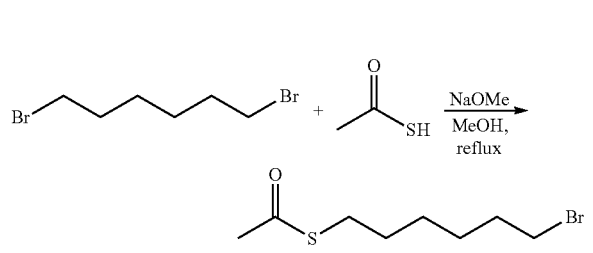

To a 100 mL three-neck round bottom flask equipped with a 50 mL dropping funnel, a reflux condenser and a gas inlet, 2.4 g (10 mmol) of 1,6-dibromohexane was added, and dissolved in 50 mL of methanol, and then degassed under argon for 1 hour. In a 50 mL two-neck round bottom flask, 0.25 g (5 mmol) of sodium methoxide and 0.37 g (5 mmol) of thioacetic acid were dissolved in 20 mL of anhydrous methanol at 0° C., and then refluxed under argon. After 1 hour, the reaction temperature was lowered to room temperature, and the reaction solution was transferred to a 50 mL dropping funnel. The reaction solution was slowly added dropwise to the flask at room temperature for 4 hours and stirred under argon for 12 hours. After completion of the reaction, methanol, which is the solvent, was removed by concentration under reduced pressure, and the yellow oil remaining in the flask was purified by column chromatography using ethyl acetate and hexane as developing solvents. Finally, S-(6-bromohexyl)ethanethioate was obtained. (1.1 g, yield: 45%)

2-1-5: Synthesis of N-butynyl-N'-methyl-2,2'-biimidazole (L-1)

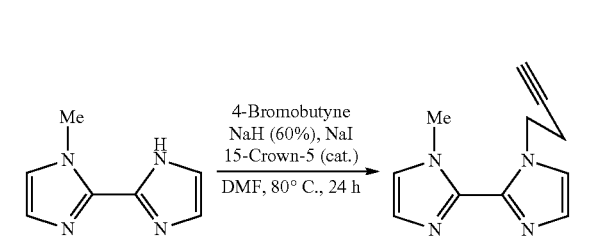

1.5 g (10 mmol) of N-methyl-2,2'-biimidazole was added to a 100 mL three-neck round-bottom flask, dissolved in 30 mL of anhydrous dimethylformamide under nitrogen, and then 0.5 g (13 mmol) of sodium hydride was added thereto. The mixture was stirred at room temperature for 1 hour, and then 1.7 g (13 mmol) of 4-bromo-1-butyne and 1.5 g (10 mmol) of sodium iodide were added thereto. The reaction solution was heated to 80° C. under nitrogen and stirred for 24 hours. The final reaction solution was cooled to room temperature, extracted with water (100 mL) and ethyl acetate (200 mL×3), and then the organic layer was collected and dried over magnesium sulfate. The organic layer was concentrated under reduced pressure to remove the solvent, and purified by column chromatography using ethyl acetate and hexane as developing solvents. Finally, N-butynyl-N'-methyl-2,2'-biimidazole was obtained. (1.5 g, yield: 74%)

2-1-6: Synthesis of N-pentynyl-N'-methyl-2,2'-biimidazole (L-2)

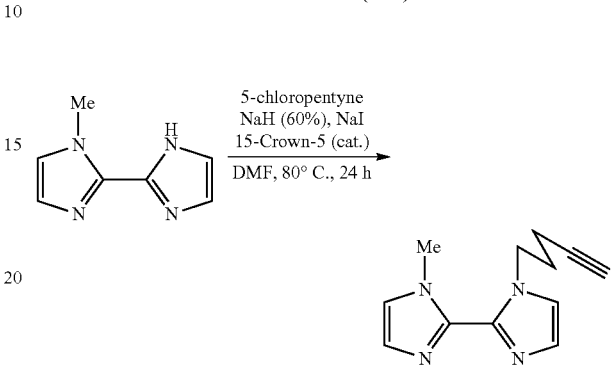

1.0 g (6.7 mmol) of N-methyl-2,2'-biimidazole was added to a 100 mL three-neck round bottom flask, dissolved in 25 mL of anhydrous dimethylformamide under nitrogen, and then 0.2 g (8.8 mmol) of sodium hydride was added thereto. The mixture was stirred at room temperature for 1 hour, and then 1.4 g (13.5 mmol) of 5-chloro-1-pentyne and 1.0 g (6.7 mmol) of sodium iodide were added. The reaction solution was heated to 80° C. under nitrogen and stirred for 24 hours. The final reaction solution was cooled to room temperature and extracted with water (100 mL) and ethyl acetate (200 mL×3). The organic layer was collected and dried over magnesium sulfate. The organic layer was concentrated under reduced pressure to remove the solvent, and purified by column chromatography using ethyl acetate and hexane as developing solvents. Finally, N-pentynyl-N'-methyl-2,2'-biimidazole was obtained. (1.2 g, 60%)

2-1-7: Synthesis of N-hexynyl-N'-methyl-2,2'-biimidazole (L-3)

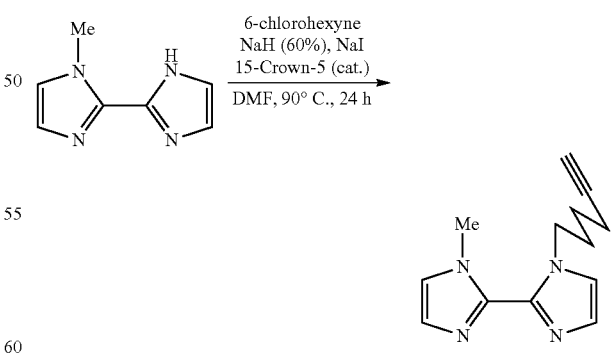

3.5 g (23.6 mmol) of N-methyl-2,2'-biimidazole was added to a 500 mL three-neck round bottom flask, dissolved in 100 mL of anhydrous dimethylformamide under nitrogen, and then 1.8 g (44.0 mmol) of sodium hydride was added thereto. The mixture was stirred at room temperature for one hour, and then 6.9 g (60.0 mmol) of 6-chloro-1-hexyne and 3.5 g (23.6 mmol) of sodium iodide were added. The reaction solution was heated to 90° C. under nitrogen and stirred for 24 hours. The final reaction solution was cooled to room temperature, extracted with water (200 mL) and ethyl acetate (300 mL×3), and the organic layer was collected and dried over magnesium sulfate. The organic layer was concentrated under reduced pressure to remove the solvent, and purified by column chromatography using ethyl acetate and hexane as developing solvents. Finally, N-hexynyl-N'-methyl-2,2'-biimidazole was obtained. (2.7 g, yield: 50%)

2-1-8: Synthesis of N-(2-(2-(2-propynyloxy)ethoxy) ethoxy)ethyl-N'-methyl-2,2'-biimidazole (L-4)

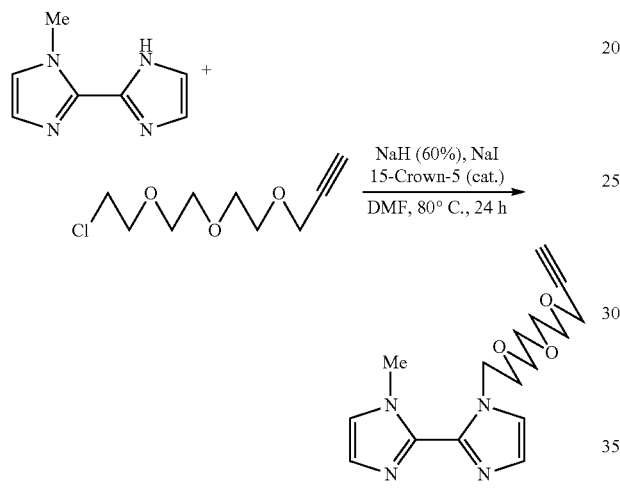

1.5 g (10.1 mmol) of N-methyl-2,2'-biimidazole was added to a 100 mL three-neck round bottom flask, dissolved in 30 mL of anhydrous dimethylformamide under nitrogen, and then 0.6 g (15.2 mmol) of sodium hydride was added thereto. The mixture was stirred at room temperature for one hour, and then 2.5 g (12.1 mmol) of (3-(2-(2-(2-chloroethoxy)ethoxy)ethoxy)propyne and 1.5 g (10.1 mmol) of sodium iodide were added. The reaction solution was heated to 90° C. under nitrogen and stirred for 24 hours. The final reaction solution was cooled to room temperature, extracted with water (200 mL) and ethyl acetate (300 mL×3), and the organic layer was collected and dried over magnesium sulfate. The organic layer was concentrated under reduced pressure to remove the solvent, and purified by column chromatography using ethyl acetate and hexane as developing solvents. Finally, N-(2-(2-(2-propynyloxy)ethoxy)ethoxy)ethyl-N'-methyl-2,2'-biimidazole was obtained. (2.0 g, yield: 60%)

2-1-9: Synthesis of S-(6-hexyl)ethanethioate-N'-methyl-2,2'-biimidazole

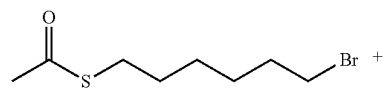

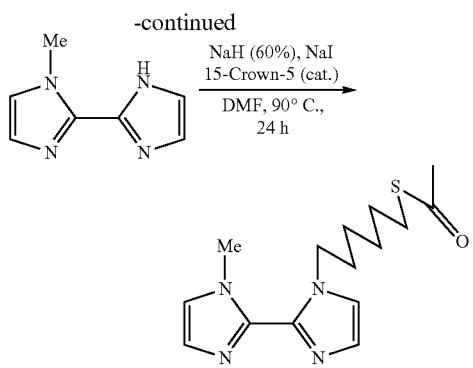

3.0 g (20.2 mmol) of N-methyl-2,2'-biimidazole was added to a 250 mL three-neck round bottom flask, dissolved in 100 mL of anhydrous dimethylformamide under nitrogen, and then 1.2 g (30.5 mmol) of sodium hydride was added thereto. The mixture was stirred at room temperature for one hour, and then 5.0 g (20.5 mmol) of S-(6-bromohexyl) ethanethioate and 3.0 g (20.2 mmol) of sodium iodide were added. The reaction solution was heated to 90° C. under nitrogen and stirred for 24 hours. The final reaction solution was cooled to room temperature, extracted with water (200 mL) and ethyl acetate (300 mL×3), and the organic layer was collected and dried over magnesium sulfate. The organic layer was concentrated under reduced pressure to remove the solvent, and purified by column chromatography using ethyl acetate and hexane as developing solvents. Finally, S-(6-hexyl)ethanethioate-N'-methyl-2,2'-biimidazole was obtained. (4.2 g, yield: 70%).

2-1-10: Synthesis of (6-hexanethiol)-N'-methyl-2,2'-biimidazole (L-5)

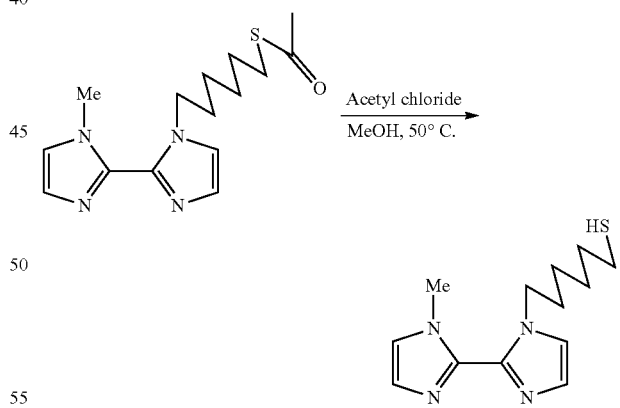

3.0 g (10.0 mmol) of S-(6-hexyl)ethanethioate-N'-methyl-2,2'-biimidazole was added to a 250 mL three-neck round bottom flask, dissolved in 100 mL of methanol, and then 40 mL of acetyl chloride was slowly added dropwise. The mixture was heated to 50° C. and stirred for 4 hours. The final reaction solution was cooled to room temperature, extracted with water (100 mL) and dichloromethane (200 mL×3), and the organic layer was collected and dried over magnesium sulfate. Finally, (6-hexanethiol)-N'-methyl-2,2'-biimidazole was obtained. (2.3 g, yield: 87%)

2-2: Synthesis of Osmium Complex

2-2-1. Synthesis of [osmium (III) (N,N'-dimethyl-2,2'-biimidazole)₂ (N-butynyl-N'-methyl-2,2'-biimidazole)](hexafluorophosphine)₃

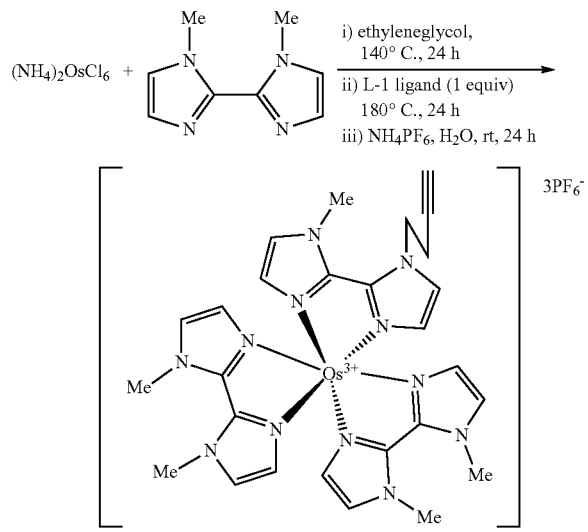

A 100 mL three-neck round-bottom flask was equipped with a reflux condenser, a gas inlet and a thermometer, and 2 g (13 mmol) of N,N'-dimethyl-2,2'-biimidazole, 3 g (6.5 mmol) of ammonium hexachloro osmate (IV) and 50 mL of ethylene glycol were stirred under argon at 140° C. for 24 hours. 1.3 g (6.5 mmol) of N-butynyl-N'-methyl-2,2'-biimidazole was dissolved in 10 mL of ethylene glycol, and then added to the reaction mixture using a syringe. The mixture was again stirred at 180° C. under argon for 24 hours. After completion of the reaction, the reaction mixture was cooled to room temperature, and the resulting red residue was removed by filtration. The filtrate was diluted with 600 mL of water, and then AG1x4 chloride resin was added and stirred for 24 hours to sufficiently oxidize in air. The solution was added dropwise to an aqueous ammonium hexafluorophosphine solution to obtain a precipitate of the ion-exchanged metal complex. The resulting solid was filtered, washed several times with water, and then dried in a vacuum oven to obtain the final compound osmium (III) complex. (5.0 g, yield: 67%) Anal. Calcd for $C_{27}H_{32}F_{18}N_{12}OsP_3$: C, 28.21; H, 2.81; N, 14.62. Found: C, 28.12; H, 3.07; N, 14.64

2-2-2: Synthesis of [osmium (III) (N,N'-dimethyl-2,2'-biimidazole)₂(N-pentynyl-N'-methyl-2,2'-biimidazole)](hexafluorophosphine)₃ (Os-2)

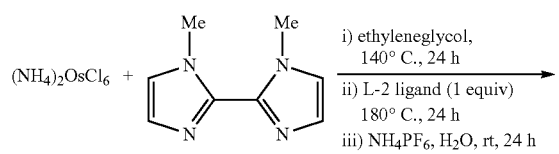

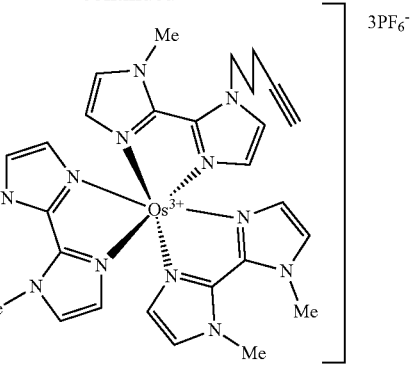

A 100 mL three-neck round-bottom flask was equipped with a reflux condenser, a gas inlet and a thermometer, and 0.7 g (4.6 mmol) of N,N'-dimethyl-2,2'-biimidazole, 1.0 g (2.3 mmol) of ammonium hexachloroosmate (IV) and 20 mL of ethylene glycol were stirred under argon at 140° C. for 24 hours. 0.5 g (2.3 mmol) of N-pentynyl-N'-methyl-2,2'-biimidazole was dissolved in 10 mL of ethylene glycol, and then added to the reaction mixture using a syringe. The mixture was again stirred at 180° C. under argon for 24 hours. After completion of the reaction, the reaction mixture was cooled to room temperature, and the resulting red residue was removed by filtration. The filtrate was diluted with 200 mL of water, and then AG1x4 chloride resin was added and stirred for 24 hours to sufficiently oxidize in air. The solution was added dropwise to an aqueous ammonium hexafluorophosphine solution to obtain a precipitate of the ion-exchanged metal complex. The resulting solid was filtered, washed several times with water, and then dried in a vacuum oven to obtain the final compound osmium (III) complex. (1.5 g, 53%) Anal. Calcd for $C_{28}H_{34}F_{18}N_{12}OsP_3$: C, 28.90; H, 2.94; N, 14.44. Found: C, 28.95; H, 3.02; N, 14.23

2-2-3: Synthesis of [osmium (III) (N,N'-dimethyl-2,2'-biimidazole)₂(N-hexynyl-N'-methyl-2,2'-biimidazole)](hexafluorophosphine)₃ (Os-3)

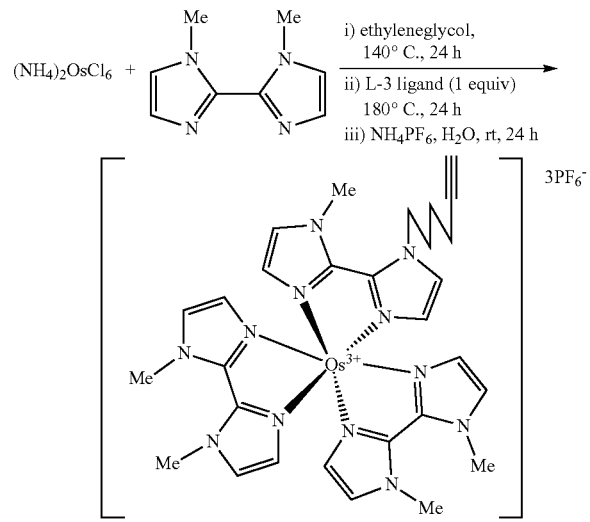

A 100 mL three-neck round-bottom flask was equipped with a reflux condenser, a gas inlet and a thermometer, and 0.4 g (2.2 mmol) of N,N'-dimethyl-2,2'-biimidazole, 0.5 g (1.1 mmol) of ammonium hexachloroosmate (IV) and 20 mL of ethylene glycol were stirred under argon at 140° C. for 24 hours. 0.3 g (1.1 mmol) of N-hexynyl-N'-methyl-2,2'-biimidazole was dissolved in 10 mL of ethylene glycol, and then added to the reaction mixture using a syringe. The mixture was again stirred at 180° C. under argon for 24 hours. After completion of the reaction, the reaction mixture was cooled to room temperature, and the resulting red residue was removed by filtration. The filtrate was diluted with 150 mL of water, and then AG1x4 chloride resin was added and stirred for 24 hours to sufficiently oxidize in air. The solution was added dropwise to an aqueous ammonium hexafluorophosphine solution to obtain a precipitate of the ion-exchanged metal complex. The resulting solid was filtered, washed several times with water, and then dried in a vacuum oven to obtain the final compound osmium (III) complex. (0.7 g, yield: 49%) Anal. Calcd for $C_{29}H_{36}F_{18}N_{12}OsP_3$: C, 29.57; H, 3.08; N, 14.27. Found: C, 29.50; H, 3.10; N, 14.27

2-2-4: Synthesis of [osmium (III) (N,N'-dimethyl-2,2'-biimidazole)$_2$(N-(2-(2-(2-propynyl-oxy)ethoxy))oxy)ethyl-N'-methyl-2,2'-biimidazole)](hexafluoro-phosphine)$_3$ (Os-4)

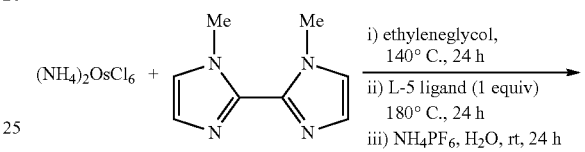

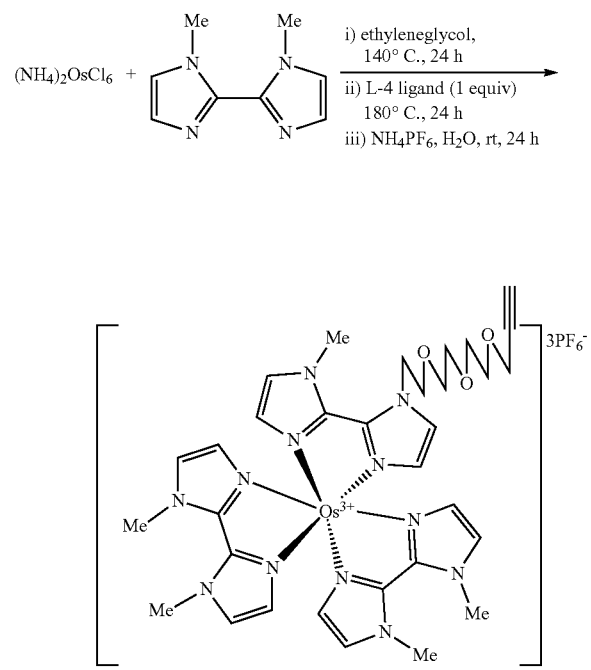

A 100 mL three-neck round-bottom flask was equipped with a reflux condenser, a gas inlet and a thermometer, and 1.5 g (9.1 mmol) of N,N'-dimethyl-2,2'-biimidazole, 2.0 g (4.6 mmol) of ammonium hexachloroosmate (IV) and 40 mL of ethylene glycol were stirred under argon at 140° C. for 24 hours. 1.5 g (4.6 mmol) of N-(2-(2-(2-propynyloxy)ethoxy)ethyl-N'-methyl-2,2'-biimidazole was dissolved in 15 mL of ethylene glycol, and then added to the reaction mixture using a syringe. The mixture was again stirred at 180° C. under argon for 24 hours. After completion of the reaction, the reaction mixture was cooled to room temperature, and the resulting red residue was removed by filtration. The filtrate was diluted with 400 mL of water, and then AG1x4 chloride resin was added and stirred for 24 hours to sufficiently oxidize in air. The solution was added dropwise to an aqueous ammonium hexafluorophosphine solution to obtain a precipitate of the ion-exchanged metal complex. The resulting solid was filtered, washed several times with water, and then dried in a vacuum oven to obtain the final compound osmium (III) complex. (2.8 g, 48%) Anal. Calcd for $C_{32}H_{42}F_{18}N_{12}O_3OsP_3$: C, 30.31; H, 3.34; N, 13.26. Found: C, 30.17; H, 3.48; N, 13.39

2-2-5: Synthesis of [osmium (III) (N,N'-dimethyl-2,2'-biimidazole)$_2$(6-hexanethiol-N'-methyl-2,2'-biimidazole)](hexafluoro-phosphine)$_3$ (Os-5)

A 100 mL three-neck round-bottom flask was equipped with a reflux condenser, a gas inlet and a thermometer, and 0.9 g (5.4 mmol) of N,N'-dimethyl-2,2'-biimidazole, 1.2 g (2.7 mmol) of ammonium hexachloroosmate (IV) and 20 mL of ethylene glycol were stirred under argon at 140° C. for 24 hours. 0.7 g (2.7 mmol) of (6-hexanethiol-N'-methyl-2,2'-biimidazole) was dissolved in 10 mL of ethylene glycol, and then added to the reaction mixture using a syringe. The mixture was again stirred at 180° C. under argon for 24 hours. After completion of the reaction, the reaction mixture was cooled to room temperature, and the resulting red residue was removed by filtration. The filtrate was diluted with 200 mL of water, and then AG1x4 chloride resin was added and stirred for 24 hours to sufficiently oxidize in air. The solution was added dropwise to an aqueous ammonium hexafluorophosphine solution to obtain a precipitate of the ion-exchanged metal complex. The resulting solid was filtered, washed several times with water, and then dried in a vacuum oven to obtain the final compound osmium (III) complex. (2.0 g, 60%) Anal. Calcd for $C_{29}H_{40}F_{18}N_{12}S_1OsP_3$: C, 28.69; H, 3.32; N, 13.85. Found: C, 28.41; H, 3.05; N, 13.61

Example 3: Synthesis of Oxidation-Reduction Polymer 3-1: Synthesis of Oxidation-Reduction Polymer (RP-1)

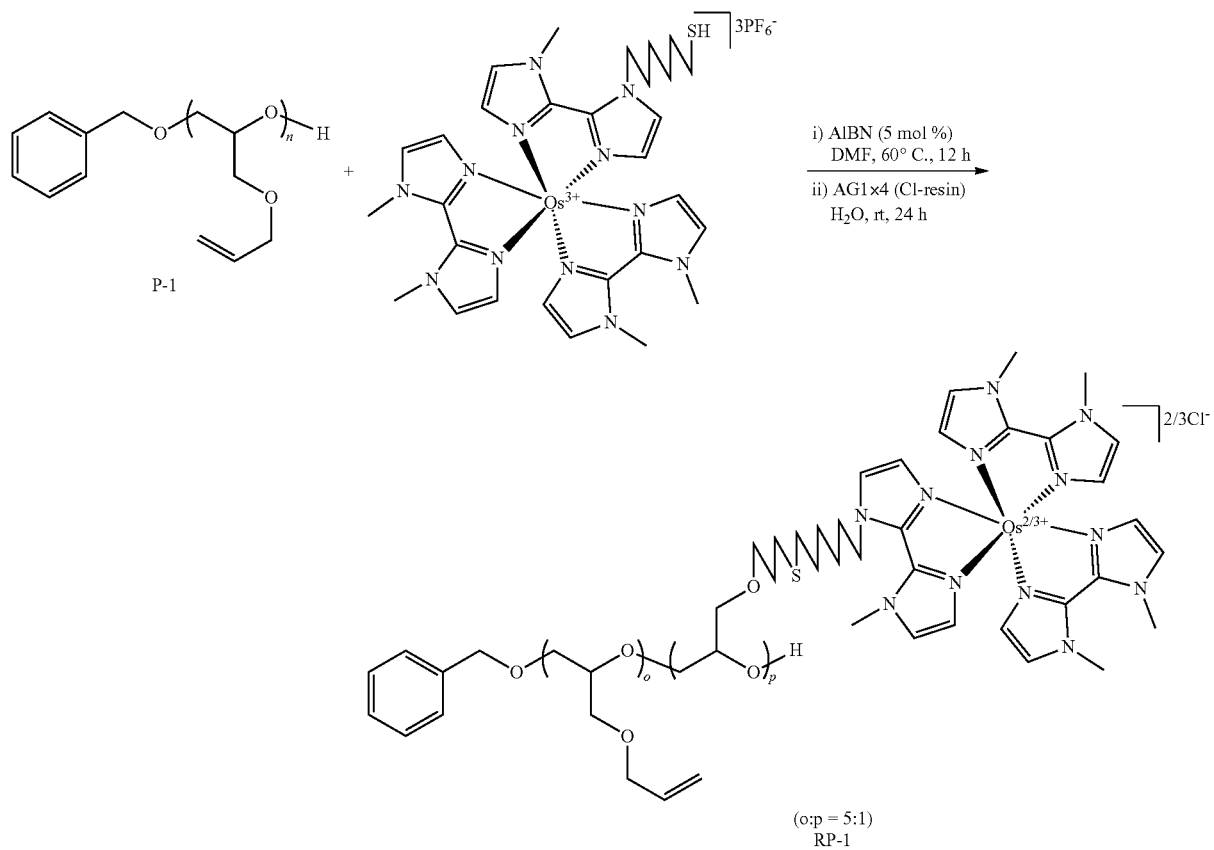

0.5 g of polymer precursor P-1 ($M_n$=10,000 g/mol) and 0.5 g of [osmium(III)(N,N'-dimethyl-2,2'-biimidazole)$_2$(6-hexanethiol-N'-methyl-2,2'-biimidazole)](hexafluorophosphine)$_3$ (Os-5) were added to a 100 mL two-neck round bottom flask, dissolved in 40 mL of dimethylformamide, and then degassed under argon for 5 minutes. 10 mg of azobi-sisobyutyronitile (AIBN) was added to the reaction mixture and stirred at 60° C. for 12 hours. After completion of the reaction, the reaction mixture was poured into ethyl acetate solution to form a precipitate. The solvent was drained off and the resulting solid was dissolved again in 80 mL of acetonitrile, and AG1x4 chloride resin and water (250 mL) were added and stirred for 24 hours. The polymer solution was concentrated under reduced pressure (50 mL), and then dialyzed to remove substances of low molecular weight (3,000 g/mol or less). The dialyzed polymer solution was lyophilized to obtain a final oxidation-reduction polymer RP-1. (0.7 g, yield: 80%)

3-2: Synthesis of Oxidation-Reduction Polymer (RP-2)

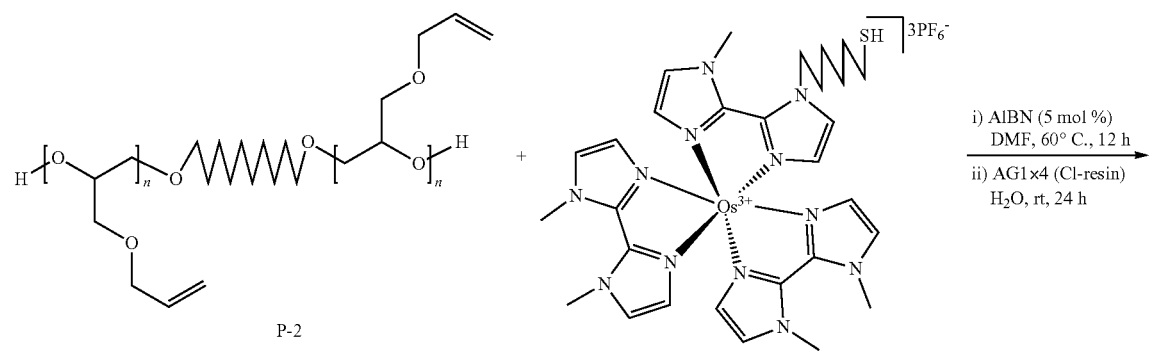

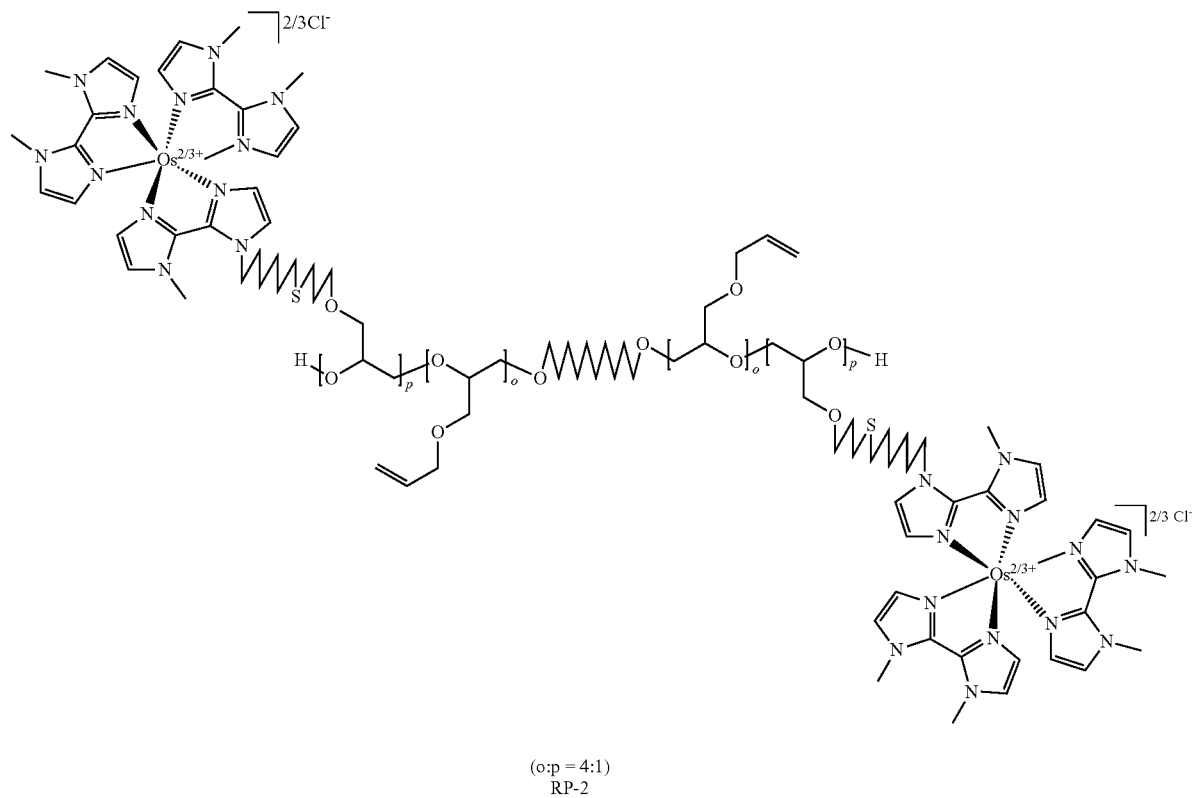

(o:p = 4:1)
RP-2

0.9 g of polymer precursor P-2 (8,800 g/mol) and 1.9 g of [osmium(III)(N,N'-dimethyl-2,2'-biimidazole)$_2$(6-hexanethiol-N'-methyl-2,2'-biimidazole)](hexafluorophosphine)$_3$ (Os-5) were added to a 250 mL two-neck round bottom flask, dissolved in 100 mL of dimethylformamide, and then degassed under argon for 5 minutes. 20 mg of azobisisobyutyronitile (AIBN) was added to the reaction mixture and stirred at 60° C. for 12 hours. After completion of the reaction, the reaction mixture was poured into ethyl acetate solution to form a precipitate. The solvent was drained off and the resulting solid was dissolved again in 100 mL of acetonitrile, and AG1x4 chloride resin and water (300 mL) were added and stirred for 24 hours. The polymer solution was concentrated under reduced pressure (50 mL), and then dialyzed to remove substances of low molecular weight (3,000 g/mol or less). The dialyzed polymer solution was lyophilized to obtain a final oxidation-reduction polymer RP-2. (2.4 g, yield: 85%)

3-3: Synthesis of Oxidation-Reduction Polymer (RP-3)

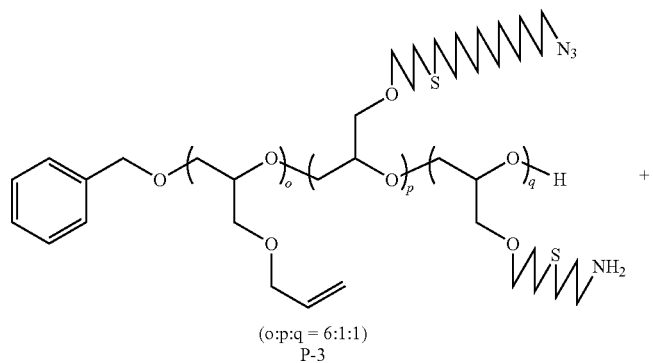

(o:p:q = 6:1:1)
P-3

-continued

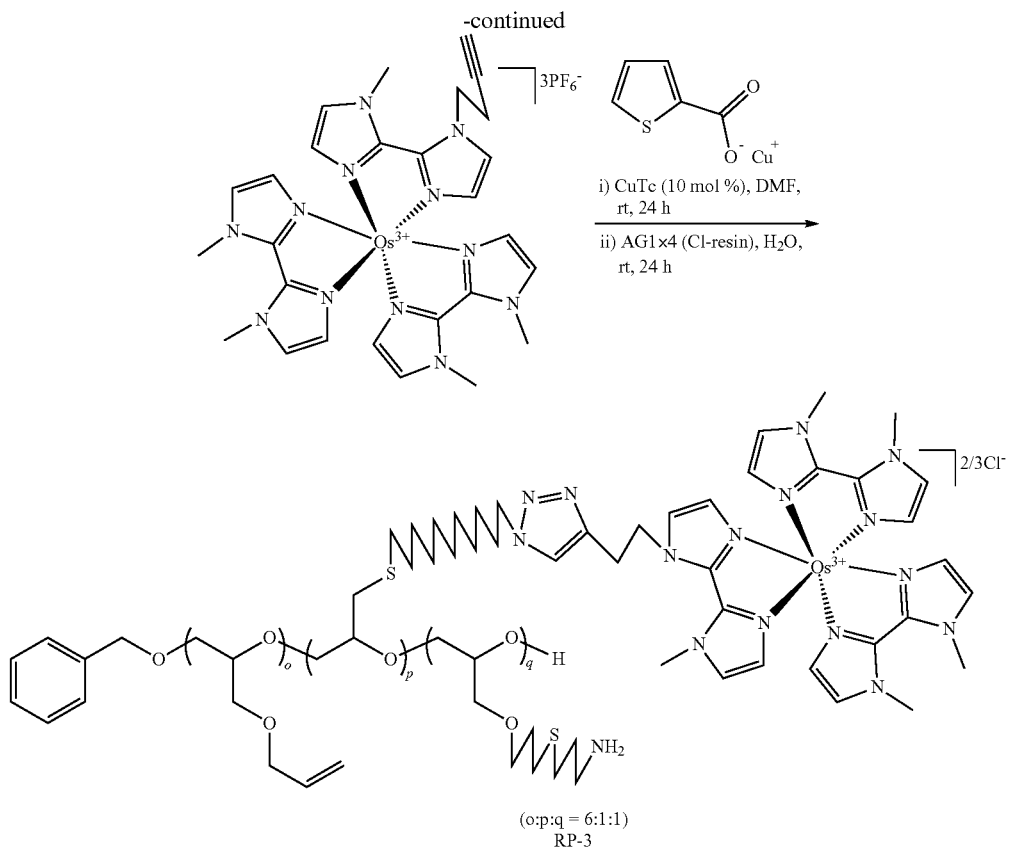

(o:p:q = 6:1:1)
RP-3

In a 100 mL two-neck round bottom flask, 0.5 g of polymer precursor P-3 was dissolved in 30 mL of dimethylformamide, and then [osmium (III) (N,N'-dimethyl-2,2'-biimidazole)$_2$(N-butynyl-N'-methyl-2,2'-biimidazole)] (hexafluorophosphine)$_3$ (Os-1) dissolved in 15 mL of dimethylformamide was added. 10 mg of a copper (I) catalyst (CuTc: copper(I) thiophene carboxylate) was added to the reaction mixture, and stirred at room temperature for 24 hours. After completion of the reaction, the reaction mixture was poured into ethyl acetate solution to form a precipitate. The solvent was drained off and the resulting solid was dissolved again in 50 mL of acetonitrile, and AG1x4 chloride resin and water (150 mL) were added and stirred for 24 hours. The polymer solution was concentrated under reduced pressure (50 mL), and then dialyzed to remove substances of low molecular weight (10,000 g/mol or less). The dialyzed polymer solution was lyophilized to obtain a final oxidation-reduction polymer RP-3. (0.6 g, yield: 75%)

Experimental Example 4: Confirmation of the Electrochemical Properties of the Oxidation-Reduction Polymer and Os Complex for an Electron Transfer Medium According to the Present Disclosure Using Cyclic Voltammetry In order to confirm the performance of the poly(allyl glycidyl ether)-based polymer and the oxidation-reduction polymer containing Os complex according to the present disclosure as an electron transfer medium, electrochemical properties were measured using the cyclic voltammetry method according to the following experimental method.

Experimental Method

① 20 mg of each of osmium complex (Os-1, 2, 3, 4, 5: PF6 anion) dissolve 20 mg was dissolved in 5 mL of 0.1 M tetrabutylammonium perchlorate acetonitrile solution, and 20 mg of each of oxidation-reduction polymer (RP-1, 2, 3: Cl anion) were dissolved in 5 mL of 0.1 M sodium chloride solution.

② Degassed with argon for 5-10 minutes to remove oxygen in the solution.

③ The working electrode, the reference electrode, and the counter electrode were connected to the oxygen-degassed solution, and changes in the electrical signal due to changes in the voltage were measured under argon.

Figure 2:
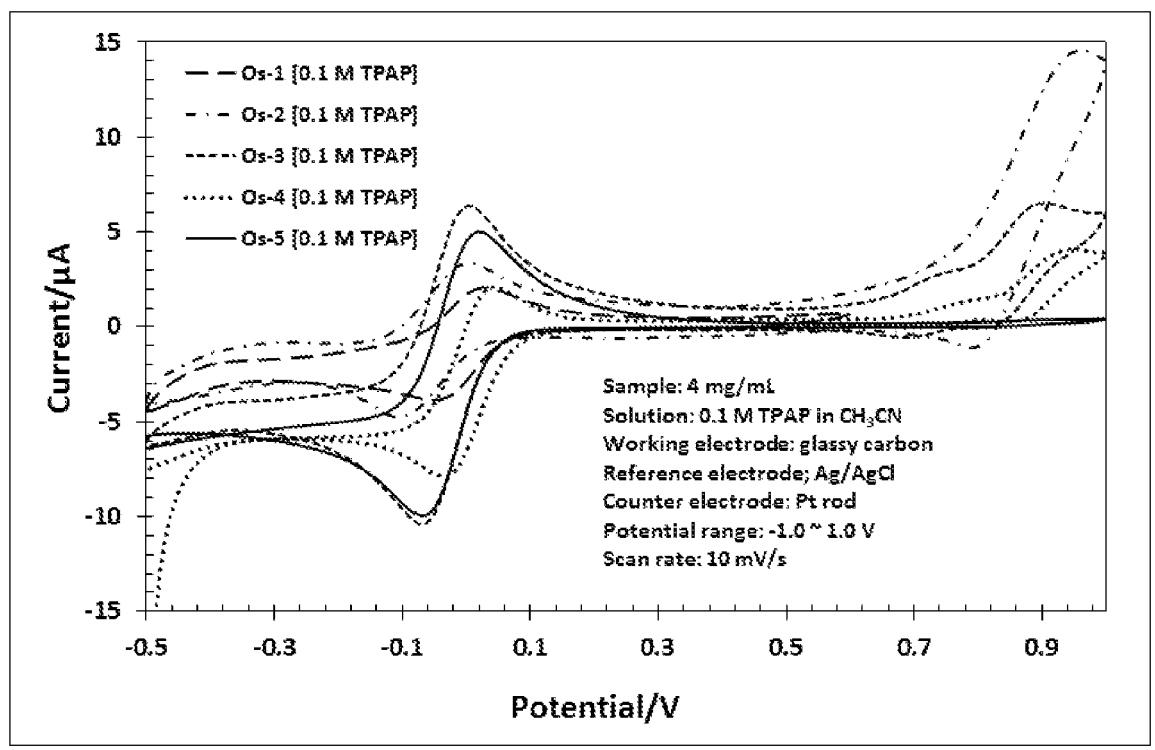
FIG. 2 is a graph measuring the performance of a simple Os complex (Os-1, Os-2, Os-3, Os-4, and Os-5) as a transfer medium using a cyclic voltammetry method.
Figure 3:
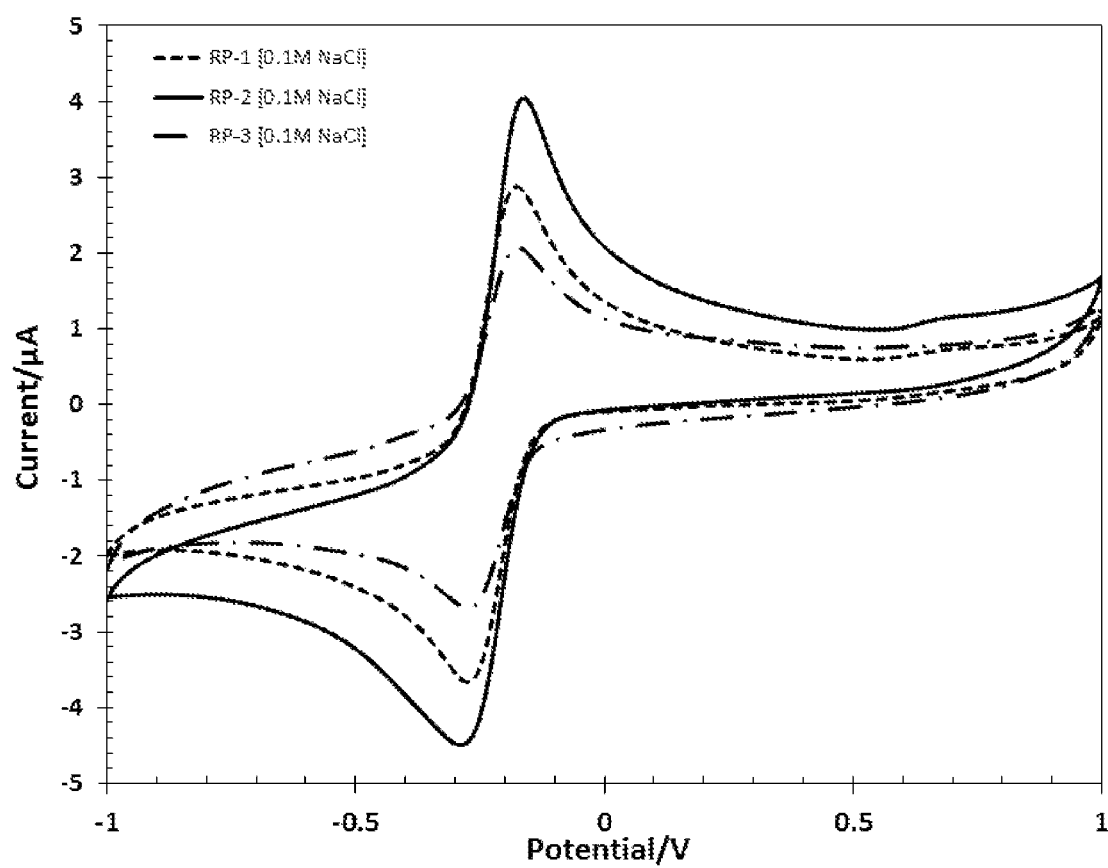
FIG. 3 is a graph in which the performance of the poly(allyl glycidyl ether)-based polymer according to the present disclosure and an oxidation-reduction polymer including Os complexes (RP-1, RP-2 and RP-3) as a transfer medium is measured by the cyclic voltammetry method.

④ The results of the experiment are shown in FIGS. 1 and 2 and Tables 1 and 2, respectively.

Experimental Materials/Conditions

Working electrode: glass carbon electrode (dia: 3.0 mm)
Reference electrode: Ag/AgCl electrode
Counter electrode: platinum rod
Test parameters
Equipment: EmStat (PalmSens Co.)
Technique: cyclic voltammetry
Potential range: −1.0~1.0 V
Scan rate: 10 mV/s

TABLE 1

| Compound | $E_{pc}$ (V) | $E_{pa}$ (V) |
|---|---|---|
| Os-1 | 0.030 | −0.035 |
| Os-2 | 0.012 | −0.097 |
| Os-3 | 0.011 | −0.066 |
| Os-4 | 0.045 | −0.026 |
| Os-5 | 0.020 | −0.060 |

TABLE 2

| Compound | $E_{pc}$ (V) | $E_{pa}$ (V) |
|---|---|---|
| RP-1 | −0.169 | −0.269 |
| RP-2 | −0.159 | −0.289 |
| RP-3 | −0.169 | −0.269 |

As shown in FIGS. 1 and 2 and Tables 1 and 2, as a result of measuring the cyclic voltammetry curve of total 5 types of osmium complexes and total 3 types of oxidation-reduction polymers, it was confirmed that the respective compounds showed an oxidation-reduction potential at approximately the same position. Therefore, it was indirectly confirmed that the performance of the oxidation-reduction polymer according to the present disclosure as an electron transport medium is the same as that of a single osmium complex.

The invention claimed is:

1. A poly (allyl glycidyl ether)-based polymer for the preparation of a oxidation-reduction polymer material, wherein a functional group selected from the group consisting of primary and secondary amine groups, an ammonium group, a halogen group, an epoxy group, an azide group, an acrylate group, an alkenyl group, an alkynyl group, a thiol group, an isocyanate, an alcohol group and a silane group is introduced into the polymer, the polymer has a structure of the following Chemical Formulas 1 or 2:

[Chemical Formula 1]

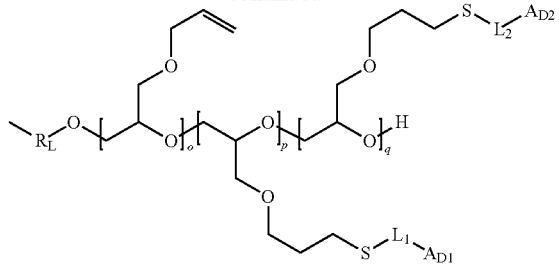

[Chemical Formula 2]

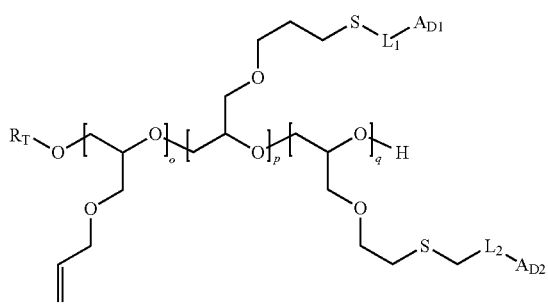

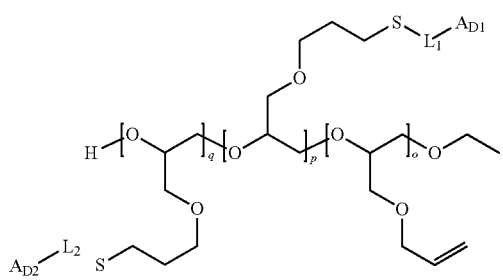

in the Chemical Formula 1 or 2, $R_T$ and $R_L$ may be each independently selected from the group consisting of a substituted or unsubstituted alkylene group having 1 to 20 carbon atoms, a substituted or unsubstituted cycloalkylene group having 1 to 20 carbon atoms, a substituted or unsubstituted ethylene glycol group having 3 to 30 carbon atoms, a substituted or unsubstituted arylene group having 6 to 30 carbon atoms, a substituted or unsubstituted heteroarylene group having 3 to 30 carbon atoms, a substituted or unsubstituted alkenyl group having 2 to 40 carbon atoms, and a substituted or unsubstituted alkynyl group having 2 to 40 carbon atoms, $L_1$ to $L_2$ are each independently selected from the group consisting of a substituted or unsubstituted alkylene group having 1 to 20 carbon atoms, a substituted or unsubstituted cycloalkylene group having 1 to 20 carbon atoms, a substituted or unsubstituted ethylene glycol group having 3 to 30 carbon atoms, a substituted or unsubstituted arylene group having 6 to 30 carbon atoms, and a substituted or unsubstituted heteroarylene group having 3 to 30 carbon atoms, $A_{D1}$ to $A_{D2}$ are selected from the group consisting of primary and secondary amine groups, an ammonium group, a halogen group, an epoxy group, an azide group, an acrylate group, an alkenyl group, an alkynyl group, thiol group, an isocyanate, an alcohol group and a silane group, o is an integer of 10 to 300;
p is an integer of 0 to 300; and
q is an integer of 10 to 300.

2. The polymer for the preparation of oxidation-reduction polymer material according to claim 1, wherein the $R_T$ and $R_L$ are each independently selected from the group of polystyrene (PS), polyethylene glycol (PEG), polyethylene oxide (PEO), polymethyl methacrylate (PMMA), polyvinylimidazole (PVI), polyvinylpyridine (PVP) and polysiloxane (PDMS), each having a molecular weight of 1,000 g/mol to 50,000 g/mol.

3. The polymer for the preparation of oxidation-reduction polymer material according to claim 1, wherein the functional group is introduced using a thiol-based compound having a functional group selected from the group consisting of primary and secondary amine groups, an ammonium group, a halogen group, an epoxy group, an azide group, an acrylate group, an alkenyl group, an alkynyl group, thiol group, an isocyanate, an alcohol group and a silane group by a click reaction.

4. The polymer for the preparation of oxidation-reduction polymer material according to claim 3, wherein the thiol-based compound is a compound of the following Chemical Formula 3, HS-L$_3$-A$_{D3}$     [Chemical Formula 3]

wherein, the $L_3$ is independently selected from the group consisting of a substituted or unsubstituted alkylene group having 1 to 20 carbon atoms, a substituted or unsubstituted cycloalkylene group having 1 to 20 carbon atoms, a substituted or unsubstituted ethylene glycol group having 3 to 30 carbon atoms, a substituted or unsubstituted arylene group having 6 to 30 carbon atoms, and a substituted or unsubstituted heteroarylene group having 3 to 30 carbon atoms, and the $A_{D3}$ is selected from the group consisting of primary and secondary amine groups, an ammonium group, a halogen group, an epoxy group, an azide group, an acrylate group, an alkenyl group, an alkynyl group, a thiol group, an isocyanate, an alcohol group and a silane group.

5. The polymer for the preparation of oxidation-reduction polymer material according to claim 1, wherein the polymer has a molecular weight of 1,000 g/mol to 50,000 g/mol.

6. An oxidation-reduction polymer material for electrochemical sensor comprising the polymer as set forth in any one of claims 1 to 5.

7. The oxidation-reduction polymer material according to claim 6, wherein a functional group selected from the group consisting of primary and secondary amine groups, an ammonium group, a halogen group, an epoxy group, an azide group, an acrylate group, an alkenyl group, an alkynyl group, a thiol group, an isocyanate, an alcohol group and a silane group, and a transition metal complex are bound to the polymer.

8. The oxidation-reduction polymer material according to claim 7, wherein the transition metal complex has a structure represented by the following Chemical Formula 4:

[Chemical Formula 4]

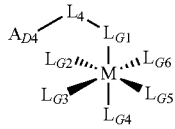

wherein,

M is a transition metal selected from the group consisting of Os, Rh, Ru, Ir, Fe and Co;

$L_{G1}$ and $L_{G2}$ are combined with each other to form a bidentate ligand selected from the following Chemical Formulas 5 to 7;

$L_{G3}$ and $L_{G4}$ are combined with each other to form a bidentate ligand selected from the following Chemical Formulas 5 to 7;

$L_{G5}$ and $L_{G6}$ are each combined with each other to form a bidentate ligand selected from the following Chemical Formulas 5 to 7;

[Chemical Formula 5]

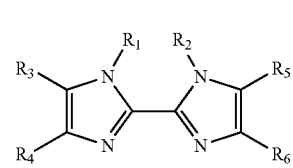

[Chemical Formula 6]

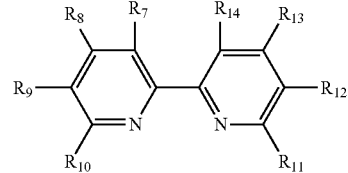

[Chemical Formula 7]

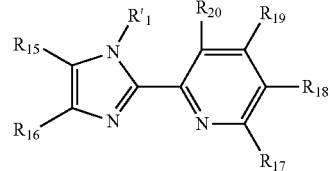

the $R_1$, $R_2$ and $R'$ are each independently selected from the group consisting of a substituted or unsubstituted alkyl group having 1 to 10 carbon atoms, a substituted or unsubstituted ethylene glycol group having 2 to 20 carbon atoms, a substituted or unsubstituted alcohol group having 1 to 20 carbon atoms, a substituted or unsubstituted alkylhalogen group having 1 to 20 carbon atoms, a substituted or unsubstituted thiol group having 1 to 20 carbon atoms, a substituted or unsubstituted alkyl azide group having 3 to 20 carbon atoms, a substituted or unsubstituted aryl azide group having 7 to 30 carbon atoms, a substituted or unsubstituted alkenyl group having 2 to 40 carbon atoms, a substituted or unsubstituted alkynyl group having 2 to 40 carbon atoms, a cyano group, a halogen group, deuterium and hydrogen, the $R_3$ to $R_{20}$ are each independently selected from the group consisting of a substituted or unsubstituted alkyl group having 1 to 10 carbon atoms, a substituted or unsubstituted cycloalkyl group having 3 to 40 carbon atoms, a substituted or unsubstituted aryl group having 6 to 50 carbon atoms, a substituted or unsubstituted heteroaryl group having 3 to 50 carbon atoms, a substituted or unsubstituted alkoxy group having 1 to 20 carbon atoms, a substituted or unsubstituted alcohol group having 1 to 20 carbon atoms, a substituted or unsubstituted alkylhalogen group having 1 to 20 carbon atoms, a substituted or unsubstituted thiol group having 1 to 20 carbon atoms, a substituted or unsubstituted alkyl azide group having 3 to 20 carbon atoms, a substituted or unsubstituted aryl azide group having 7 to 30 carbon atoms, a substituted or unsubstituted aryloxy group having 6 to 30 carbon atoms, a substituted or unsubstituted alkylamino group having 1 to 20 carbon atoms, a substituted or unsubstituted arylamino group having 6 to 30 carbon atoms, a substituted or unsubstituted alkylsilyl group having 1 to 20 carbon atoms, a substituted or unsubstituted arylsilyl group having 6 to 30 carbon atoms, a substituted or unsubstituted arylalkylamino group having 1 to 50 carbon atoms, a substituted or unsubstituted alkenyl group having 2 to 40 carbon atoms, a substituted or unsubstituted alkynyl group having 2 to 40 carbon atoms, a cyano group, a halogen group, deuterium and hydrogen;

the $L_4$ is independently selected from the group consisting of a substituted or unsubstituted alkylene group having 1 to 20 carbon atoms, a substituted or unsubstituted cycloalkylene group having 1 to 20 carbon atoms, a substituted or unsubstituted ethylene glycol group having 2 to 30 carbon atoms, a substituted or unsubstituted arylene group having 6 to 30 carbon atoms, and a substituted or unsubstituted heteroarylene group having 3 to 30 carbon atoms, and the $A_{D4}$ is selected from the group consisting of an azide group, an acrylate group, an alkenyl group, an alkynyl group, a thiol group, isocyanate, an alcohol group and a silane group.

9. The oxidation-reduction polymer material according to claim 7, wherein the transition metal complex is functionalized with a functional group selected from the group consisting of an amine group, an ammonium group, a halogen group, an epoxy group, an azide group, an acrylate group, an alkenyl group, an alkynyl group, a thiol group, an isocyanate, an alcohol group, and a silane group.

10. The oxidation-reduction polymer material according to claim 9, wherein the functionalized transition metal complex has a structure of the following Chemical Formula 8a, 8b or 8c:

[Chemical Formula 8a]

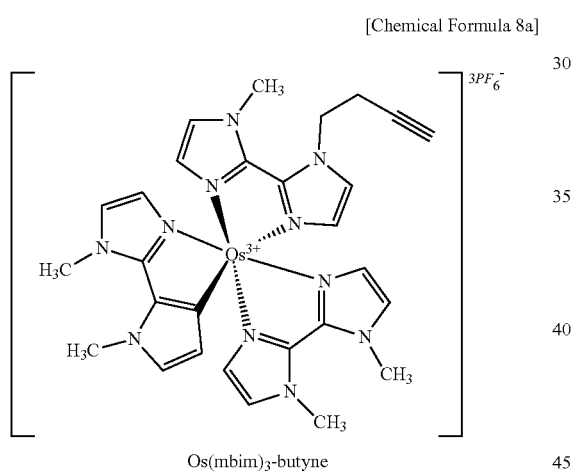

Os(mbim)$_3$-butyne

[Chemical Formula 8b]

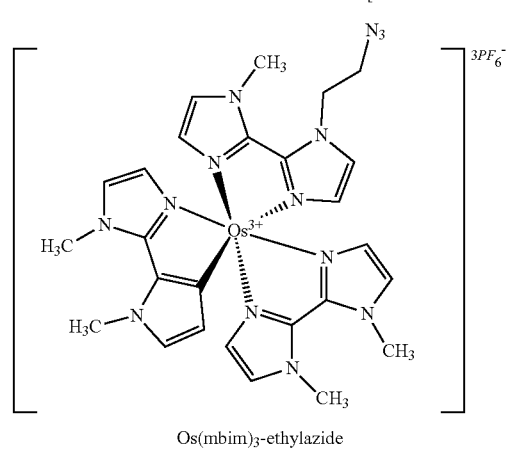

Os(mbim)$_3$-ethylazide

[Chemical Formula 8c]

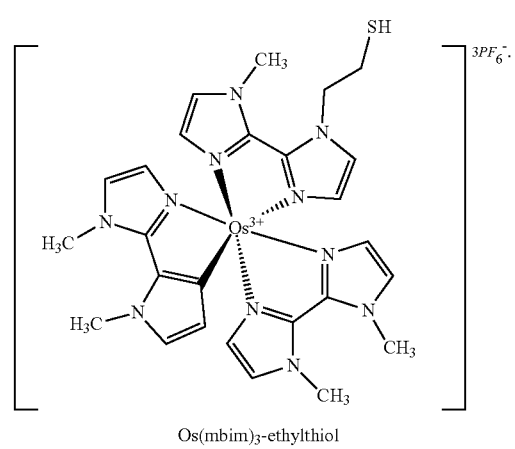

Os(mbim)$_3$-ethylthiol

11. The oxidation-reduction polymer material according to claim 7, having a structure of the following Chemical Formula 9 or 10:

[Chemical Formula 9]

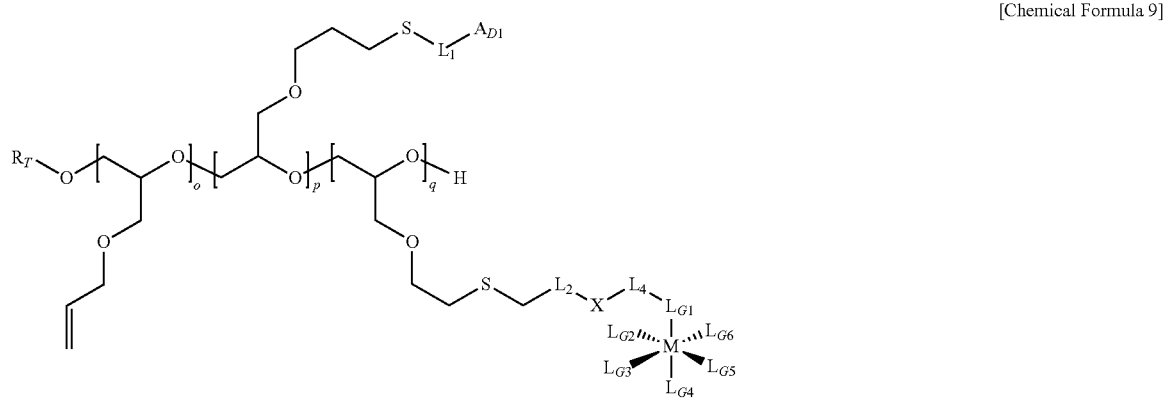

-continued

[Chemical Formula 10]

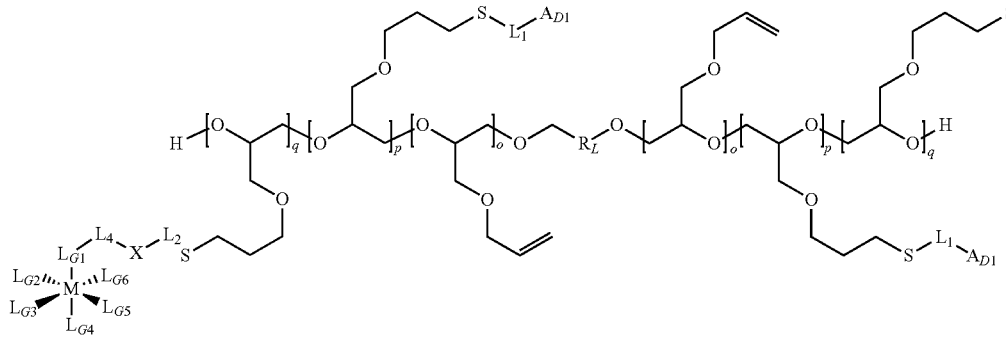

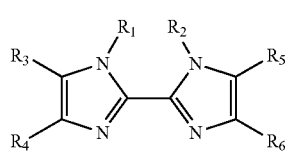

in the Chemical Formula 9 or 10,

- $R_T$ and $R_L$ are each independently selected from the group consisting of a substituted or unsubstituted alkylene group having 3 to 20 carbon atoms, a substituted or unsubstituted cycloalkylene group having 6 to 20 carbon atoms, a substituted or unsubstituted ethylene glycol group having 2 to 30 carbon atoms, a substituted or unsubstituted arylene group having 6 to 30 carbon atoms, a substituted or unsubstituted heteroarylene group having 3 to 30 carbon atoms, a substituted or unsubstituted alkenyl group having 2 to 40 carbon atoms and a substituted or unsubstituted alkynyl group having 2 to 40 carbon atoms,
- $L_1$ to $L_2$ are each independently selected from the group consisting of a substituted or unsubstituted alkylene group having 1 to 20 carbon atoms, a substituted or unsubstituted cycloalkylene group having 1 to 20 carbon atoms, a substituted or unsubstituted ethylene glycol group having 3 to 30 carbon atoms, a substituted or unsubstituted arylene group having 6 to 30 carbon atoms, and a substituted or unsubstituted heteroarylene group having 3 to 30 carbon atoms,
- $A_{D1}$ is selected from the group consisting of primary and secondary amine groups, an ammonium group, a halogen group, an epoxy group, an azide group, an acrylate group, an alkenyl group, an alkynyl group, a thiol group, isocyanate, an alcohol group and a silane group,
- o is an integer of 0 to 300;
- p is an integer of 0 to 300;
- q is an integer of 10 to 300;
- M is a transition metal selected from the group consisting of Os, Rh, Ru, Ir, Fe, and Co;
- $L_{G1}$ and $L_{G2}$ are combined with each other to form a bidentate ligand selected from Chemical Formulas 5 to 7;
- $L_{G3}$ and $L_{G4}$ are each combined with each other to form a bidentate ligand selected from Chemical Formulas 5 to 7; and
- $L_{G5}$ and $L_{G6}$ are each combined with each other to form a bidentate ligand selected from Chemical Formulas 5 to 7,

[Chemical Formula 5]

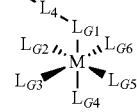

[Chemical Formula 6]

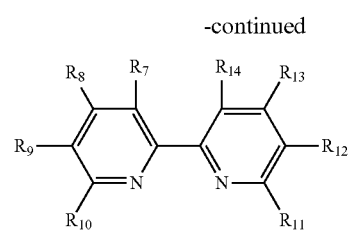

[Chemical Formula 7]

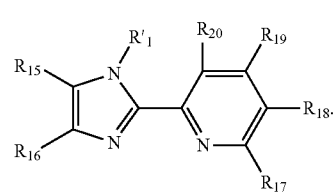

the $R_1$, $R_2$ and $R'_1$ are each independently selected from the group consisting of a substituted or unsubstituted alkyl group having 1 to 10 carbon atoms, a substituted or unsubstituted ethylene glycol group having 2 to 20 carbon atoms, a substituted or unsubstituted alcohol group having 1 to 20 carbon atoms, a substituted or unsubstituted alkylhalogen group having 1 to 20 carbon atoms, a substituted or unsubstituted thiol group having 1 to 20 carbon atoms, a substituted or unsubstituted alkyl azide group having 3 to 20 carbon atoms, a substituted or unsubstituted aryl azide group having 7 to 30 carbon atoms, a substituted or unsubstituted alkenyl group having 2 to 40 carbon atoms, a substituted or unsubstituted alkynyl group having 2 to 40 carbon atoms, a cyano group, a halogen group, deuterium and hydrogen, the $R_3$ to $R_{20}$ are each independently selected from the group consisting of a substituted or unsubstituted alkyl group having 1 to 10 carbon atoms, a substituted or unsubstituted cycloalkyl group having 3 to 40 carbon atoms, a substituted or unsubstituted aryl group having 6 to 50 carbon atoms, a substituted or unsubstituted heteroaryl group having 3 to 50 carbon atoms, a substituted or unsubstituted alkoxy group having 1 to 20 carbon atoms, a substituted or unsubstituted alcohol group having 1 to 20 carbon atoms, a substituted or unsubstituted alkylhalogen group having 1 to 20 carbon atoms, a substituted or unsubstituted thiol group having 1 to 20 carbon atoms, a substituted or unsubstituted alkyl azide group having 3 to 20 carbon atoms, a substituted or unsubstituted aryl azide group having 7 to 30 carbon atoms, a substituted or unsubstituted aryloxy group having 6 to 30 carbon atoms, a substituted or unsubstituted alkylamino group having 1 to 20 carbon atoms, a substituted or unsubstituted arylamino group having 6 to 30 carbon atoms, a substituted or unsubstituted alkylsilyl group having 1 to 20 carbon atoms, a substituted or unsubstituted arylsilyl group having 6 to 30 carbon atoms, a substituted or unsubstituted arylalkylamino group having 1 to 50 carbon atoms, a substituted or unsubstituted alkenyl group having 2 to 40 carbon atoms, a substituted or unsubstituted alkynyl group having 2 to 40 carbon atoms, a cyano group, a halogen group, deuterium and hydrogen;

the $L_4$ is independently selected from the group consisting of a substituted or unsubstituted alkylene group having 1 to 20 carbon atoms, a substituted or unsubstituted cycloalkylene group having 1 to 20 carbon atoms, a substituted or unsubstituted ethylene glycol group having 2 to 30 carbon atoms, a substituted or unsubstituted arylene group having 6 to 30 carbon atoms, and a substituted or unsubstituted heteroarylene group having 3 to 30 carbon atoms, and X is a functional group selected from the group consisting of a triazole group, ether, thiol ether, an amide group, an urea group, an urethane group and a silane group.

12. A method for producing the oxidation-reduction polymer material as set forth in claim 6 comprising the steps of:

(a) polymerizing allyl glycidyl ether in the presence of an initiator to prepare a polyallyl-glycidyl ether-based polymer precursor; and (b) introducing a functional group selected from the group consisting of an amine group, an ammonium group, a halogen group, an epoxy group, an azide group, an acrylate group, an alkenyl group, an alkynyl group, a thiol group, isocyanate, an alcohol group, and a silane group, and a transition metal complex into the polymer precursor prepared in step (a).

13. A method for manufacturing an electron transport medium comprising the steps of: coating the poly (allyl glycidyl ether)-based oxidation-reduction polymer material as set forth in claim 6 onto an electrode and then curing the coated electrode.

14. An electron transport medium which is manufactured by the method as set forth in claim 13.

15. An electrochemical biosensor comprising the electron transport medium which is manufactured by the method as set forth in claim 13.

16. A sensing layer for an electrochemical biosensor comprising an enzyme capable of subjecting a liquid biological sample to an oxidation-reduction reaction; and the electron transport medium which is manufactured by the method as set forth in claim 13.

17. The sensing layer for an electrochemical biosensor according to claim 16, further comprising a carbon nanotube.

18. An electrochemical biosensor comprising the sensing layer for an electrochemical biosensor as set forth in claim 16.

* * * * *